(12) United States Patent
Bilodeau-Goeseels et al.

(10) Patent No.: US 6,967,090 B2
(45) Date of Patent: Nov. 22, 2005

(54) NUCLEIC ACID AND PROTEIN SEQUENCES OF BOVINE EPIDERMAL GROWTH FACTOR

(75) Inventors: Sylvie Bilodeau-Goeseels, Lethbridge (CA); Sushil Jacob John, Lethbridge (CA); Leonard Brent Selinger, Lethbridge (CA); Bernhard F. Benkel, Lethbridge (CA)

(73) Assignee: Her Majesty the Queen in right of Canada, as represented by the Minister of Agriculture and Agri-Food, Lethbridge (CA)

( * ) Notice: Subject to any disclaimer, the term of this patent is extended or adjusted under 35 U.S.C. 154(b) by 71 days.

(21) Appl. No.: 10/150,648

(22) Filed: May 17, 2002

(65) Prior Publication Data

US 2003/0059802 A1 Mar. 27, 2003

Related U.S. Application Data

(60) Provisional application No. 60/292,136, filed on May 18, 2001.

(51) Int. Cl.$^7$ .................. C12P 21/06; C12N 15/04; C12N 5/02; C07K 14/00
(52) U.S. Cl. .................. 435/69.1; 435/320.1; 435/325; 435/410; 530/350; 530/399
(58) Field of Search .................. 435/69.1, 320.1, 435/325, 410; 530/350, 399

(56) References Cited

U.S. PATENT DOCUMENTS

| | | | |
|---|---|---|---|
| 5,059,586 A | * 10/1991 | Collier et al. | .................. 514/12 |
| 5,096,825 A | 3/1992 | Barr et al. | .................. 435/255 |
| 5,753,622 A | 5/1998 | Buret et al. | .................. 514/12 |
| 5,785,990 A | 7/1998 | Langrehr | .................. 424/442 |

FOREIGN PATENT DOCUMENTS

| | | | | |
|---|---|---|---|---|
| JP | 2104293 | 4/1990 | ........... | C12P/21/02 |
| WO | WO 88/04180 | 6/1988 | ........... | A61K/37/36 |
| WO | WO 92/16626 | 3/1992 | ........... | C12N/15/16 |

OTHER PUBLICATIONS

Hideo, O., Akimasa, M., Yasushi, M., Kazuhide, O., Shigaki, K., Takeshi, K. and Kazuyuki, T. (1997) Rabbit epithelial cell growth factor. Database JPOP Online, Database accession No. E50021.

Salmanian, A.H., Gushchin, A., Medvedeva, T, Noori–Daloil, M.R. and Domansky. N. (1996) Synthesis and expression of the gene for human epidermal growth factor in transgenic potato plants. Biotechnology Letters 18(9):1095–1098.

Bell, G.I., Fong. N.M., Stempien. M.M., Wormsted, M.A., Caput, D., Ku, L., Urdea, M.S., Rail, L.B. and Sanchez-Pescador, R. (1986) Human epidermal growth factor precursor: cDNA sequence, expression in vitro and gene organization. Nucleic Acids Res. 14: 8427–8446.

Benkel, B.F. and Fong, Y. (1996) Long range–inverse PCR (LR–IPCR): extending the useful range of inverse PCR. Genetic Analysis. Biomol. Eng. 13: 123–127.

Buret, A., Gall, D.G., Olson, M.E., and Hardin, J.A. (1997) Anti–infective properties of a muscosal cytokine: epidermal growth factor (EGF). Proc. Agric. Biotechnol Workshop, AARI, p. 19.

Buret, A., Olson, M.E., Gall, D.G. and Hardin, J.A. (1998) Effects of orally administered epidermal growth factor on enteropathogenic *Escherichia coli* infection in rabbits. Infection and Immunity 66(10):4917–4923.

Carpenter, G. and Cohen, S. (1979) Epidermal growth factor. Ann. Rev. Biochem. 48: 193–216.

Clare, J. J., Romanos, M.A., Rayment, F.B., Rowedder, J.E. Smith, M.A., Payne, M.M., Sreekrishna, K. and Henwood, C.A. (1991) Production of mouse epidermal growth factor in yeast: high–level secretion using *Pichia pastoris* strains containing multiple gene copies Gene 105: 205–212.

Cooke, R.M., Wilkinson, A.J., Baron, M., Pastore, A., Tappin, M.J., Campbell, I.D., Gregory, H. and Sheard, B. (1987) The solution structure of human epidermal growth factor. Nature 327: 339–341.

Donovan, S.M. and Odle, J. (1994) Growth factors in milk as mediators of infant development. Ann. Rev. Nutr. 14: 147–167.

Fisher, D. (2000) Hybrid fold recognition: combining sequence derived properties with evolutionary information. Pacific Symp. Biocomputing, Hawaii, 119–130, Jan. 2000, World Scientific.

Gray, A., Dull, T.J. and Ulinch, A. (1983) Nucleotide sequence of epidermal growth factor cDNA predicts a 128,000–molecular weight protein precursor. Nature 303: 722–725.

Hollenberg, M.D. and Gregory, H. (1980) Epidermal growth factor–urogastrone: biological activity and receptor binding of derivatives. Mol. Pharmacol. 17: 314–320.

(Continued)

*Primary Examiner*—Janet Andres
(74) *Attorney, Agent, or Firm*—Greenlee, Winner And Sullivan, P.C.

(57) ABSTRACT

The invention provides a nucleotide sequence of bovine epidermal growth factor (bEGF) and the deduced amino acid sequence of the encoded protein. The invention further provides the nucleotide sequence of mature bEGF and the deduced mature bEGF protein. The invention extends to homologous nucleic acids, proteins, and fragments functionally equivalent to the nucleotide sequence of the bEGF gene and bEGF protein, respectively. Bovine EGF may be expressed in microorganisms such as *E. coli* or *P. pastoris*, and plant hosts, such as potato. Activity of recombinant bEGF may be confirmed using a cell proliferation/DNA synthesis assay. Bovine EGF demonstrates utility in livestock and dairy productions as a supplement in farm animal feed to promote growth; to prevent or treat intestinal infections; to stimulate precocious maturation of gut cells to secrete an appropriate spectrum of digestive enzymes; and to increase nutrient absorption.

16 Claims, 5 Drawing Sheets

OTHER PUBLICATIONS

Kim, J.G., Vallet, J.L. and Christenson. R.K. (2001) Characterization of uterine epidermal growth factor during pregnancy in pigs. Domestic Animal Endocrinology 20(4): 253–265.

Miller, S.A. Dykes, D.D. and Polesky. H.F. (1988) A simple salting out procedure for extracting DNA from human nucleated cells Nucleic Acids Res. 16: 1215.

Nasim. M.T., Jaenicke, S., Belduz, A., Kollmus, H., Flohe, L. and McCarthy. J.E. (2000) Eukaryotic selenocystein incorporation follows a nonprocessive mechanism that competes with translational termination. J. Biol. Chem. 275: 14846–14852.

Ochman, H., Gerber, A.S. and Hartl, D.L. (1988) Genetic applications of an inverse polymerase chain reaction. Genetics 120: 621–623.

Pascall, J.C., Jones, D.S.C., Doel, S.M., Clements, J.M., Hunter, M., Fallon, T., Edwards, M. and Brown, K.D. (1991) Cloning and characterization of a gene encoding pig epidermal growth factor. J. Mol. Endocrin. 6:63–70.

Saggi, S.J., Safirstein, R. and Price, P.M. (1992) Cloning and sequencing of the rat preproepidermal growth factor cDNA: comparison with mouse and human sequences. DNA Cell Biol. 11: 481–487.

Shin, S.Y., Watanabe, M., Kako, K., Ohtaki, T. and Munekata, E. (1994) Structure–activity relationship of human epidermal growth factor (h–EGF). Life Science 55: 131–139.

Simpson, R.J., Smith, J.A., Mortiz, R.L., O'Hare, M.J., Rudland, P.S., Morrison, J.R., Lloyd, C.J., Grogo, B., Burgess, A.W. and Nice, E.C. (1985) Rat epidermal growth factor: complete amino acid sequence. Homology with the corresponding murine and human proteins; isolation of a form truncated at both ends with full in vitro biological activity. Eur. J. Biochem. 153: 629–637.

Stewart, F., Powel, C.A., Lennard, S.N., Allen, W.R., Amet, L. and Edwards, R.M. (1994) Identification of the horse epidermal growth factor (EGF) coding sequence and its use in monitoring EGF gene expression in the endometrium of the pregnant mare. J. Mol. Endo. 12: 341–350.

Stone, N.E., Schmutz, J.J., Shang, J., Cox, D.R. and Myers, R.M. Homo sapiens chromosome 4 clone B207D4 map 4q25, complete sequence. Genbank Accession No. AC004050. submitted Jan. 28, 1998.

Tadaki, D.K. and Niyogi, S.K. (1993) The functional importance of hydrophobicity of the tyrosine at position 13 of human epidermal growth factor in receptor binding. J. Biol. Chem. 268: 10114–10119.

Tate, W.P., Mansell, J.B., Mannering, S.A., Irvine, J.H., Major, L.L. and Wilson, D. N. (1999) UGA: a dual signal for 'stop' and for recoding in protein synthesis. [Review]. Biochemistry 64(12): 1342–1353.

van Rooijen, G.J.H. and Moloney, M.M. (1995, Plant seed oil–bodies as carriers for foreign proteins Bio/Technology 13: 72–77.

Zijlstra, R.T., Odle, J., Hall, W.F., Petschow, B.W., Gelberg, H.B. and Litov, R.E. (1994) Effect of orally administered epidermal growth factor on intestinal recovery of neonatal pigs infected with rotavirus. J. Ped. Gastroent. Nutr. 19: 382–390.

* cited by examiner

```
              ....|....| ....|....| ....|....| ....|....| ....|....|
                  10         20         30         40         50

BOVINE        GATATTGATG AGTGCCGACG GGGCGTGCAC AGCTGTGGGG AAAATGCCAC
MURINE        GATATTGACG AGTGCCAGCG GGGGGCGCAC AACTGCGCTG AGAATGCCGC
PORCINE       GATATTGATG AGTGCCAACT AGGTGTGCAC ACCTGTGGGG AAAATGCCAC
HUMAN         GATATTGATG AGTGCCAACT GGGGGTGCAC AGCTGTGGAG AGAATGCCAG

....|....| ....|....| ....|....| ....|....| ....|....|
                  60         70         80         90        100

BOVINE        CTGAACAAAT ATGGAGGGAA ACCACACTTG CACGTGTGCT GGCGACTTGT
MURINE        CTGCACCAAC ACGGAGGGAG GCTACAACTG CACCTGCGCA GGCCGCCCAT
PORCINE       CTGTACAAAT ACGGAGGGAA ACTACACCTG CACATGTGCT GGCCGCCCCT
HUMAN         CTGCACAAAT ACAGAGGGAG GCTATACCTG CATGTGTGCT GGACGCCTGT

....|....| ....|....| ....|....| ....|....| ....|....|
                 110        120        130        140        150

BOVINE        CTGAGCCTGG ACAGATTTGC CCTGACTCTA CTCTGCTGTC TCACCTTGGG
MURINE        CCTCGCCCGG ACGGAGTTGC CCTGACTCTA CCGCACCCTC TCTCCTTGGG
PORCINE       CTGAACCCGG ACGGATTTGC CCTGACCCTA CTCCACCCTC TCACCTCGGG
HUMAN         CTGAACCAGG ACTGATTTGC CCTGACTCTA CTCCACCCCC TCACCTCAGG

....|....| ....|....| ....|....| ....|....| ....|....|
                 160        170        180        190        200

BOVINE        AAGAATGGGC ACAATTTT-- -TTGAAAAAA TGTTTCCCTG AATATACCCC
MURINE        GAAGATGGCC ACCATTTG-- -GACCGAAAT AGTTATCCAG GATGCCCATC
PORCINE       GAGGATGGCC GCTATTCT-- -GTGAGAAAT AGTTACTCTG AATGCCCGCC
HUMAN         GAAGATGACC ACCACTATTC CGTAAGAAAT AGTGACTCTG AATGTCCCCT

....|....| ....|....| ....|....| ....|....| ....|....|
                 210        220        230        240        250

BOVINE        GAATTTTGAA GGGTACTGCC TCAATGGTCG TGTCTGTATA TATTTTGGCA
MURINE        CTCATATGAT GGATACTGCC TCAATGGTGG CGTGTGCATG CATATTGAAT
PORCINE       GTCCCACGAC GGGTACTGCC TCCACGGTGG TGTGTGTATG TATATTGAAG
HUMAN         GTCCCACGAT GGGTACTGCC TCCATGATGG TGTGTGCATG TATATTGAAG
```

FIG. 1A

```
                  ....|....| ....|....| ....|....| ....|....| ....|....|
                      260        270        280        290        300
BOVINE        TTGCCAACCT GTTCTCCTGC CACTGTCCCA TTGGCTACCC TGGGAAGCGA
MURINE        CACTGGACAG CTACACATGC AACTGTGTTA TTGGCTATTC TGGGGATCGA
PORCINE       CCGTCGACAG CTATGCCTGC AACTGTGTTT TTGGCTACGT TGGCGAGCGA
HUMAN         CATTGGACAA GTATGCATGC AACTGTGTTG TTGGCTACAT CGGGGAGCGA

....|....| ....|....| ....|....| ....|....| ....|....|
                      310        320        330        340        350
BOVINE        GGTGAGTACA TAGACTTCGA TGGGTGGGAT CCGCACAGTG CAGGCCGTGG
MURINE        TGTCAGACTC GAGACCTACG ATGGTGGGAG CTGCGTCATG CTGGCTACGG
PORCINE       TGTCAGCACA GAGACTTGAA ATGGTGGGAG CTGCGCCACG CTGGCCTCGG
HUMAN         TGTCAGTACC GAGACCTGAA GTGGTGGGAA CTGCGCCACG CTGGCCACGG

....|....| ....|....| ....|....| ....|....| ....|....|
                      360        370        380        390        400
BOVINE        GCATCAGTGG AACACCAGCC CGGTGGCTGT CCGTGCGCTG GTGCTGGCTT
MURINE        GCAGAAGCAT GACATCATGG TGGTGGCTGT CTGCATGGTG TCACTGGTCC
PORCINE       GCGACAGTGG AACGTCACGG TGGTGGCCGT CTGCGTGGTG GTGCTGGTCC
HUMAN         GCAGCAGCAG AAGGTCATCG TGGTGGCTGT CTGCGTGGTG GTGCTTGTCA

....|....| ....|....| ....|....| ....|...
                      410        420        430
BOVINE        TCCTGCTGCT CCTCGGGCTG TGCAGAGCTC ACTACTAC
MURINE        TGCTGCTCCT CTTGGGGATG TGGGGGACTT ACTACTAC
PORCINE       TGCTGCTGCT CCTGGGGCTG TGGGGGGCTC ACTACTAC
HUMAN         TGCTGCTCCT CCTGAGCCTG TGGGGGGCCC ACTACTAC
```

BOVINE              AAATGTTTCC CTGAATATAC CCCGAATTTT GAAGGGTACT GCCTCAATGG
MURINE              AATAGTTATC CAGGATGCCC ATCCTCATAT GATGGATACT GCCTCAATGG
PORCINE             AATAGTTACT CTGAATGCCC GCCGTCCCAC GACGGGTACT GCCTCCACGG
HUMAN               AATAGTGACT CTGAATGTCC CCTGTCCCAC GATGGGTACT GCCTCCATGA

....|....| ....|....| ....|....| ....|....| ....|....|
                         60         70         80         90        100

BOVINE              TCGTGTCTGT ATATATTTTG GCATTGCCAA CCTGTTCTCC TGCCACTGTC
MURINE              TGGCGTGTGC ATGCATATTG AATCACTGGA CAGCTACACA TGCAACTGTG
PORCINE             TGGTGTGTGT ATGTATATTG AAGCCGTCGA CAGCTATGCC TGCAACTGTG
HUMAN               TGGTGTGTGC ATGTATATTG AAGCATTGGA CAAGTATGCA TGCAACTGTG

....|....| ....|....| ....|....| ....|....| ....|....|
                         110        120        130        140        150

BOVINE              CCATTGGCTA CCCTGGGAAG CGAGGTGAGT ACATAGACTT CGATGGGTGG
MURINE              TTATTGGCTA TTCTGGGGAT CGATGTCAGA CTCGAGACCT ACGATGGTGG
PORCINE             TTTTTGGCTA CGTTGGCGAG CGATGTCAGC ACAGAGACTT GAAATGGTGG
HUMAN               TTGTTGGCTA CATCGGGGAG CGATGTCAGT ACCGAGACCT GAAGTGGTGG

....|....
BOVINE              GATCCGCAC
MURINE              GAGCTGCGT
PORCINE             GAGCTGCGC
HUMAN               GAACTGCGC
```

BOVINE       DIDECRRGVH SCGENATZTN MEGNHTCTCA GDLSEPGQIC PDSTLLSHLG
MURINE       DIDECQRGAH NCAENAACTN TEGGYNCTCA GRPSSPGRSC PDSTAPSLLG
PORCINE      DIDECQLGVH TCGENATCTN TEGNYTCTCA GRPSEPGRIC PDPTPPSHLG
HUMAN        DIDECQLGVH SCGENASCTN TEGGYTCMCA GRLSEPGLIC PDSTPPPHLR

....|....| ....|....| ....|....| ....|....| ....|....|
                 60         70         80         90        100

BOVINE       KN-GHNFLKK CFPEYTPNFE GYCLNGRVCI YFGIANLFSC HCPIGYPGKR
MURINE       ED-GHHLDRN SYPGCPSSYD GYCLNGGVCM HIESLDSYTC NCVIGYSGDR
PORCINE      ED-GRYSVRN SYSECPPSHD GYCLHGGVCM YIEAVDSYAC NCVFGYVGER
HUMAN        EDDHHYSVRN SDSECPLSHD GYCLHDGVCM YIEALDKYAC NCVVGYIGER

....|....| ....|....| ....|....| ....|....| ....|.
                110        120        130        140

BOVINE       GEYIDFDGWD PHSAGRGHQW NTSPVAVRAL VLAFLLLLGL CRAHYY
MURINE       CQTRDLRWWE LRHAGYGQKH DIMVVAVCMV SLVLLLLGM WGTYYY
PORCINE      CQHRDLKWWE LRHAGLGRQW NVTVVAVCVV VLVLLLLGL WGAHYY
HUMAN        CQYRDLKWWE LRHAGHGQQQ KVIVVAVCVV VLVMLLLSL WGAHYY
```

BOVINE       KCFPEYTPNF  EGYCLNGRVC  IYFGIANLFS  CHCPIGYPGK  RGEYIDFDGW  DPH
MURINE       NSYPGCPSSY  DGYCLNGGVC  MHIESLDSYT  CNCVIGYSGD  RCQTRDLRWW  ELR
PORCINE      NSYSECPPSH  DGYCLHGGVC  MYIEAVDSYA  CNCVFGYVGE  RCQHRDLKWW  ELR
HUMAN        NSDSECPLSH  DGYCLHDGVC  MYIEALDKYA  CNCVVGYIGE  RCQYRDLKWW  ELR
```

FIG. 4

NUCLEIC ACID AND PROTEIN SEQUENCES OF BOVINE EPIDERMAL GROWTH FACTOR

CROSS REFERENCE TO RELATED APPLICATIONS

This application claims priority from U.S. Provisional Patent Application No. 60/292,136, filed May 18, 2001. To the extent that it is consistent herewith, the aforementioned application is incorporated herein by reference.

FIELD OF THE INVENTION

The invention pertains to nucleic acid and protein sequences of bovine epidermal growth factor.

BACKGROUND OF THE INVENTION

In recent years, a highly competitive market place and environmental concerns have , encouraged researchers to develop technologies to improve the efficiency of livestock and dairy productions. However, a greater public awareness of animal welfare issues and of food production indicates that further improvement in efficiency may have to be achieved without compromising animal health and well-being. Recent findings in a number of animal systems suggest that epidermal growth factor (EGF) may be used in livestock and dairy productions as a feed additive to stimulate precocious maturation of gut cells to secrete an appropriate spectrum of digestive enzymes; increase nutrient absorption; and prevent or treat intestinal infection.

Derived from a precursor protein of about 1,200 amino acids, EGF is a 6 kDa polypeptide composed of 53 amino acids (Carpenter and Cohen, 1979). It is naturally present in saliva, intestinal secretions, and other bodily fluids, and is produced in large quantities in colostrum and milk (Donovan and Odle, 1994). EGF stimulates the growth and maturation of the human fetal stomach. Due to high EGF concentrations in the colostrum of most species, and the presence of EGF receptors within the intestine, EGF (and other growth factors) have been proposed to also contribute to early postnatal gastrointestinal development (Donovan and Odle, 1994).

EGF may be involved in regulating nutrient uptake. In the rodent, EGF increases electrolytes, glucose and proline transport across jejunal brush-border membranes. In the piglet, EGF promotes maturation of gut cell function by enhancing both sucrase and maltase activity without any marked effect on lactase and alkaline phosphatase activities (International Publication No. WO 88/04180 to Wilson et al.). Use of EGF as a feed additive for growth promotion is thus advantageous.

Enteric colibacillosis or scour is a bacterial infection caused by the pathogen *Escherichia coli*. Common in newborn and young farm animals, scour has considerable impact upon the agricultural economy. Overcrowding of young animals in confined areas is commonly followed by outbreaks of scour, which is characterized by diarrhea, dehydration, and eventual death. Dairy calves receiving milk replacer are more susceptible to scour than those fed cow's milk, with a morbidity rate due to infection of up to 75%.

Since a vaccine for scour is presently lacking, an effective treatment such as EGF is desirable. Supplementation with EGF improves intestinal functions of piglets infected with rotavirus (Zijlstra et al., 1994). Further, oral EGF administration reduces the rate of enteric infections in rabbits and prevents the reduction in weight gain caused by infection (Buret et al., 1997). U.S. Pat. No. 5,753,622 to Buret et al. discloses methods for treating scour and other pathogenic infections, and for increasing weight gain by administration of EGF orally or indirectly in animal feed. In most of these previous studies, EGF from a species different from the recipient was used; however, in principle, EGF of the same species would be preferable to avoid undesirable side effects. For use in dairy or beef cattle production, it is thus preferable to use bovine EGF (bEGF).

A feed additive or supplement must be economical to be widely adopted by producers. Due to advances in molecular biology and recombinant DNA technology, large quantities of foreign proteins for research, therapeutic, and industrial applications are efficiently produced. Genes coding for desired proteins can be transferred from organisms impractical for production into microbial, plant, or animal expression systems, with microbes most commonly used for expression of heterologous proteins due to their ease of growth and genetic manipulation. Human EGF has been expressed in yeast at a rate of 40 ng/mg of protein (U.S. Pat. No. 5,096,825 to Barr et al.), while mouse EGF has been produced by the yeast *Pichia pastoris* at a rate of 450 µg/ml of medium (Clare et al., 1991).

Complementary DNA sequences encoding the mature EGF protein have been previously cloned from mouse, rat, pig, horse and human (Gray et al., 1983; Simpson et al., 1985; Kim et al., 2001; Stewart et al., 1994; Bell et al., 1986). The deduced amino acid sequences show 55% to 85% identity to each other, with striking conservation of key structural residues, particularly three glycines (residues 18, 36, and 39), six cysteines (residues 6, 14, 20, 31, 33, and 42), and tyrosine 37. The variation in other residues presumably accounts for the very low cross-reactivity between species observed with antisera and nucleic acid probes. The cDNA sequence encoding the precursor protein has been cloned from human, pig, and mouse.

Although cDNA sequences encoding the mature EGF protein have been previously cloned from various sources as previously described, the DNA sequences encoding the mature EGF protein have not previously been obtained from a bovine source. However, bEGF may benefit dairy and beef cattle production by promoting growth; preventing or treating intestinal infections; increasing nutrient absorption; and accelerating development of immature gut cells. For such potential commercial applications, use of EGF from a bovine source itself is desired to avoid undesirable side effects which may compromise animal health and well-being. There is thus a need to obtain the DNA sequences encoding the mature bEGF protein and to produce bEGF successfully in a recombinant system.

In general, the homology between human and bovine sequences allows the use of human probes or primers to obtain the corresponding bEGF DNA sequence. However, sequences for the bEGF DNA and protein sequences were found to be very different from those of other species, which accounts for the initial difficulties in attempting to clone the bEGF DNA sequence, and explains why this sequence had not yet been successfully cloned despite the many promising commercial applications of such an invention.

SUMMARY OF THE INVENTION

The invention provides DNA sequences encoding bovine epidermal growth factor (bEGF), and the sequence of the encoded proteins. A portion of the DNA sequence of the bEGF gene and the deduced amino acid sequence of the encoded bEGF protein are depicted in SEQ ID NOS: 8 and 9, respectively. The DNA sequence for the mature bEGF protein and the deduced amino acid sequence of the mature bEGF protein are provided in SEQ ID NOS: 10 and 11, respectively.

Thus, the invention broadly provides an isolated nucleic acid encoding a polypeptide for bEGF, wherein the encoded polypeptide comprises an amino acid sequence selected from a) an amino acid sequence depicted in SEQ ID NO: 9;

b) an amino acid sequence depicted in SEQ ID NO: 11; and c) a functionally equivalent amino acid sequence having at least 55%, more preferably at least 60%, more preferably at least 65%, more preferably at least 70%, more preferably at least 75%, more preferably at least 80%, more preferably at least 85%, more preferably at least 90%, more preferably at least 95% and most preferably at least 99% homology, to the amino acid sequence depicted in SEQ ID NO: 9 or to the amino acid sequence depicted in SEQ ID NO: 11. The invention extends to fragments of the isolated polypeptide for bovine epidermal growth factor, wherein the fragments comprise functionally equivalent polypeptides as the amino acid sequence depicted in SEQ ID NO: 11.

In another aspect of the invention, there is provided an isolated nucleic acid encoding a polypeptide for bEGF, wherein the nucleic acid comprises the nucleotide sequence selected from a) a nucleotide sequence depicted in SEQ ID NO: 8;

b) a nucleotide sequence depicted in SEQ ID NO: 10; and c) a functionally equivalent nucleotide sequence having at least 75%, more preferably at least 80%, more preferably at least 85%, more preferably at least 90%, more preferably at least 95%, and most preferably at least 99% homology to the nucleotide sequence depicted in SEQ ID NO: 8 or to the nucleotide sequence depicted in SEQ ID NO: 10. The invention extends to fragments of isolated nucleic acids encoding polypeptides for bEGF, wherein the fragments comprise functionally equivalent nucleotide sequences as the nucleotide sequence depicted in SEQ ID NO: 10.

In another broad aspect, the invention provides vectors and cells comprising a nucleic acid molecule encoding the bEGF polypeptide, and methods for producing the encoded polypeptide.

The invention extends to expression constructs constituting a nucleic acid encoding bEGF operably linked to control sequences capable of directing expression of bEGF in a suitable host.

The invention further extends to host cells which have been transformed with, and express DNA encoding the bEGF polypeptide, and to methods of producing such transformed host cells.

The invention further extends to monoclonal and polyclonal antibodies raised against the bEGF polypeptide or fragments thereof.

The bEGF polypeptide or functionally equivalent fragments thereof may be used in livestock and dairy productions as a supplement in farm animal feed to promote growth; to prevent or treat intestinal infections, particularly enteropathogenic *E. coli* infections such as enteric colibacillosis; giardiasis; and scour; to increase nutrient absorption; and to stimulate precocious maturation of gut cells to secrete an appropriate spectrum of digestive enzymes.

In another broad aspect, the invention provides a method for improving the growth of an animal and a method for preventing and treating intestinal infection of an animal by administering the bEGF polypeptide. The invention thus provides a feed additive comprising a preparation selected from a) a polypeptide for bEGF encoded by a nucleic acid;

b) a polypeptide for bEGF encoded by a nucleic acid, wherein the polypeptide for bEGF is in combination with inert or active ingredients;

c) a microorganism or a plant tissue, wherein the microorganism or the plant tissue expresses a polypeptide for bEGF encoded by a nucleic acid; and d) a culture medium or an extract obtained from the microorganism or the plant tissue, wherein the culture medium or the extract contains a polypeptide for bEGF encoded by a nucleic acid.

In yet another broad aspect, the invention provides a feed composition comprising a feedstuff combined or treated with a bEGF polypeptide encoded by a nucleic acid for bEGF.

As used herein and in the claims, the terms and phrases set out below have the following definitions.

"Antibodies" includes monoclonal and polyclonal antibodies.

"Bovine" refers to species of the Subfamily Bovinae, which includes *Bison bison* (Bison, Buffalo), *Bison bonasus* (European Bison or Wisent), *Bos frontalis* (Gayal), *Bos indicus* (Zebu), *Bos taurus* (Domestic Cow), *Boselaphus tragocamelus, Bubalus bubalis* (Water Buffalo), *Syncerus caffer* (African Buffalo, Cape Buffalo), *Taurotragus derbianus, Taurotragus oryx* (Common Eland), *Tragelaphus angasii* (Nyala), *Tragelaphus eurycerus, Tragelaphus imberbis* (Lesser Kudu), *Tragelaphus scriptus* (Bushbuck), *Tragelaphus spekii* (Sitatunga), *Tragelaphus strepsiceros* (Greater Kudu).

"Circularization" means the alignment of the ends of a linearized DNA and their ligation to form a covalently closed circular molecule or "circular DNA."

"Coding sequence" means the part of a gene which codes for the amino acid sequence of a protein, or for a functional RNA such as a tRNA or rRNA.

"Complement" or "complementary sequence" means a sequence of nucleotides which forms a hydrogen-bonded duplex with another sequence of nucleotides according to Watson-Crick base-pairing rules. For example, the complementary base sequence for 5'-AAGGCT-3" is 3'-TTCCGA-5'.

"Conventional polymerase chain reaction" means a technique by which target DNA fragments are amplified in an exponential manner, whereby primers are designed to hybridize to opposite strands of DNA and extension proceeds inwards across the two primers.

"Degenerate" or "degeneracy" means a property of the genetic code whereby more than one codon can specify a particular amino acid.

"Downstream" means on the 3' side of any site in DNA or RNA.

"Enteric colibacillosis" means an infection caused by enterotoxigenic (toxin producing) *E. coli* strains. The *E. coli* strains adhere and multiply in large numbers on the surface of the small intestine, and secrete the enterotoxins which cause severe digestive alterations leading to clinical diarrhea, dehydration and high mortality rates.

"Enteropathogenic" means tending to produce disease in the intestinal tract.

"Exon" means the segment of a eukaryotic gene which codes for a specific domain of a protein.

"Expression" means the transcription of a gene into structural RNA (rRNA, tRNA) or messenger RNA (mRNA) with subsequent translation into a protein.

An amino acid sequence that is "functionally equivalent" to bEGF is an amino acid sequence which has been modified by single or multiple amino acid substitutions, by addition and/or deletion of amino acids, or where one or more amino acids have been chemically modified, but which nevertheless retains the activity of bEGF. "Functionally equivalent" nucleotide sequences are those which encode polypeptides having substantially the same biological activity as bEGF.

"Giardiasis" means an infestation with or disease caused by a flagellate protozoan (genus *Giardia*) which is often characterized by diarrhea.

Two nucleic acid sequences are "heterologous" to one another if the sequences are derived from separate organisms, whether or not such organisms are of different species, as long as the sequences do not naturally occur together in the same arrangement in the same organism.

Two polynucleotides or polypeptides are "homologous" or "identical" if the sequence of nucleotides or amino acid residues, respectively, in the two sequences is the same when aligned for maximum correspondence as described herein. Sequence comparisons between two or more polynucleotides or polypeptides are generally performed by comparing portions of the two sequences over a comparison window to identify and compare local regions of sequence similarity. The comparison window is generally from about 20 to about 200 contiguous nucleotides or contiguous amino acid residues. The "percentage of sequence identity" or "percentage of sequence homology" for polynucleotides and polypeptides may be determined by comparing two optimally aligned sequences over a comparison window, wherein the portion of the polynucleotide or polypeptide sequence in the comparison window may include additions or deletions (i.e., gaps) as compared to the reference sequence (which does not comprise additions or deletions) for optimal alignment of the two sequences. The percentage is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. A list providing sources of both commercially available and free software is found in Ausubel et al. (1990). Readily available sequence comparison and multiple sequence alignment algorithms are, respectively, the Basic Local Alignment Search Tool (BLAST) (Altschul et al., 1997) and ClustalW programs. Other suitable programs include GAP, BESTFIT, FASTA, and TFASTA in the Wisconsin Genetics Software Package (Genetics Computer Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTP program, available as described above.

As discussed in greater detail hereinafter, homology between nucleotide sequences can also be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology.

"Host cell" includes an animal, a plant, a yeast, a fungal, a protozoan and a prokaryotic host cell.

"Intestinal infection" is meant to include, but is not limited to, enteropathogenic *E. coli* infections such as enteric colibacillosis; giardiasis; and scour.

"Intron" means an intervening sequence in a gene. It is transcribed but excised before the mRNA is translated.

"Inverse polymerase chain reaction" means a technique used to amplify unknown DNA sequences flanking a core region of known sequences, whereby the DNA is digested with appropriate restriction enzymes and circularized, and primers are designed such that extension proceeds outwards and the product contains sequences upstream and downstream of the known sequences.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein.

"Livestock" is meant to include, for example, dairy and beef cattle, pigs, goats, and sheep. The term is meant to include young and adult animals.

A "polynucleotide" or "nucleic acid" means a linear sequence of deoxyribonucleotides (in DNA) or ribonucleotides (in RNA) in which the 3' carbon of the pentose sugar of one nucleotide is linked to the 5' carbon of the pentose sugar of the adjacent nucleotide via a phosphate group. The "polypeptide" or "nucleic acid" may comprise DNA, including cDNA, genomic DNA, and synthetic DNA, or RNA, which may be double-stranded or single-stranded, and if single-stranded, may be the coding strand or non-coding (anti-sense) strand.

A "polynucleotide construct" means a nucleic acid molecule which is isolated from a naturally occurring gene or which has been modified to contain segments of nucleic acid which are combined and juxtaposed in a manner which would not otherwise exist in nature.

Two DNA sequences are "operably linked" if the nature of the linkage does not interfere with the ability of the sequences to effect their normal functions relative to each other. For instance, a promoter region would be operably linked to a coding sequence if the promoter were capable of effecting transcription of that coding sequence.

A "polypeptide" means a linear polymer of amino acids that are linked by peptide bonds.

"Promoter" means a cis-acting DNA sequence, generally 80–120 base pairs long and located upstream of the initiation site of a gene, to which RNA polymerase may bind and initiate correct transcription.

A "recombinant" nucleic acid molecule, for instance a recombinant DNA molecule, means a novel nucleic acid sequence formed in vitro through the ligation of two or more nonhomologous DNA molecules (for example a recombinant plasmid containing one or more inserts of foreign DNA cloned into its cloning site or its polylinker).

"Scour" means prolonged diarrhea in animals.

"Silent changes" means inclusion, for example, of changes which do not alter the amino acid sequence encoded by the polynucleotide.

"Transformation" means the directed modification of the genome of a cell by the external application of purified recombinant DNA from another cell of different genotype, leading to its uptake and integration into the subject cell's genome. In bacteria, the recombinant DNA is not integrated into the bacterial chromosome, but instead replicates autonomously as a plasmid.

A "transgenic" means an organism into which foreign DNA has been introduced into the germ line.

A "transgenic plant" encompasses all descendants, hybrids, and crosses thereof, whether reproduced sexually or asexually, and which continue to harbour the foreign DNA, and is meant to include transgenic plants, plant tissues, and plant cells.

"Upstream" means on the 5' side of any site in DNA or RNA.

A "variant" or "variation" of a gene means nucleotide sequences which encode for the same protein or which code for equivalent proteins having bEGF activity.

A "variant" or "variation" of a protein means variants (including derivatives or analogs) of the bEGF protein or fragments thereof. Such variants may differ in amino acid sequence from the bEGF protein by one or more substitutions, additions, deletions, fusions, and truncations, which may be present in any combination.

A "vector" means a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include, but are not limited to, phage, cosmid, baculovirus, retroviral, and plasmid vectors.

BRIEF DESCRIPTION OF THE DRAWINGS

FIGS. 1A and 1B are a sequence alignment of portions of DNA coding sequences of the bovine EGF (SEQ ID NO: 8), with corresponding EGF sequences from mouse, pig, and human. The sources of the EGF sequences are:
1) mouse (Gray et al., 1983; GenBank accession no. J00380) nucleotides 3108–3539, SEQ ID 18 NO: 24;
2) pig (Kim et al., 2001; GenBank accession no. AF336151) nucleotides 3172 to 3606, SEQ ID NO: 25; and
3) human (Bell et al., 1986; GenBank accession no. X04571) nucleotides 3170–3607, SEQ ID NO: 26.

FIG. 2 shows the alignment of the DNA coding sequences for the mature bEGF protein (SEQ ID NO: 10) with the corresponding mouse (nucleotides 3282 to 3440, SEQ ID NO: 27), pig (nucleotides 3346 to 3504, SEQ ID NO: 28), and human sequences (nucleotides 3347 to 3505, SEQ ID NO: 29).

FIG. 3 shows the alignment of the deduced bEGF protein sequence (SEQ ID NO: 9) with the corresponding mouse (residues 919 to 1063, SEQ ID NO: 30), pig (residues 912 to 1056, SEQ ID NO: 31), and human (residues 912 to 1057, SEQ ID NO: 32) EGF protein sequences.

FIG. 4 is the alignment of the deduced mature bEGF protein (SEQ ID NO: 11) with the corresponding mouse (residues 977 to 1029, SEQ ID NO: 33), pig (residues 970 to 1022, SEQ ID NO: 34), and human (residues 970 to 1022, SEQ ID NO: 35) mature EGF proteins.

DESCRIPTION OF THE PREFERRED EMBODIMENTS

EGF is a small polypeptide of 53 amino acids which is produced from a much larger precursor protein. The precursor protein is encoded by a gene spanning 110 kb of DNA where 24 short exons are separated by introns of various size. Upon excision of the introns, an mRNA of approximately 4,700 base pairs is produced which encodes the precursor protein of approximately 1,200 amino acids. The mature human EGF protein is produced by excision of amino acid residues 977 to 1029 of the precursor protein which are encoded by the last 95 nucleotides at the 3' end of exon 20 and by the first 64 nucleotides at the 5' end of exon 21 which correspond to nucleic acids 3347–3505 of the mRNA (Bell et al., 1986).

I. Nucleic Acid and Polypeptide Sequences for bEGF

Genomic DNA is initially isolated from bovine blood (Example 1). To proceed with cloning of the sequences encoding bEGF, primers of SEQ ID NOS: 1 and 2 in the presence of bovine total genomic DNA are used in a polymerase chain reaction (PCR) (Example 2). The primer of SEQ ID NO: 1 encompasses nucleotides 3215–3237 of the human EGF cDNA sequence and thus lies upstream of the sequences encoding the mature EGF protein. This primer is designed such that the potential degeneracies are accommodated by mixing nucleotide bases. Also degenerate, the primer of SEQ ID NO: 2 encompasses nucleotides 3377–3400 of the human EGF cDNA sequence and is therefore within the mature region. With these two primers, a 1456 base pair fragment (SEQ ID NO: 3) is obtained which is cloned and sequenced. The fragment has significant homology to mouse and human EGF DNA sequences, containing 56 base pairs of exon 19, a 1320 base pair intron, and 80 base pairs of exon 20, including 30 base pairs encoding the first ten amino acids at the $NH_2$ terminus of the mature EGF protein, as shown by searches of DNA and protein databases for similarities using version 2.0 of the BLAST algorithm (Altschul et al., 1997).

The inventors' initial strategy to clone the DNA sequences encoding the remainder of the mature EGF protein was to use a bovine specific 5' primer designed from the sequence obtained above and a 3' primer designed from the sequence of other species downstream of the mature region; however, this strategy was unsuccessful since many tested primer combinations could not anneal to and amplify bEGF sequences. It was thus suspected that the bEGF sequences downstream from the mature region would not allow successful amplification when using primers designed from the sequence of other species. Inverse PCR, which amplifies unknown flanking sequences, was then used. In conventional PCR, primers are designed to hybridize to opposite strands of DNA and extension proceeds inwards across the two primers. In inverse PCR, the DNA is circularized and primers are designed such that the extension proceeds outwards and the product contains sequences upstream and downstream of the known sequences (Ochman et al., 1988; Benkel and Fong, 1996).

To amplify DNA sequences upstream and downstream of bEGF sequences obtained above, bovine genomic DNA is digested with specific restriction enzymes in separate reactions, then diluted to a low concentration, and ligated (Example 3). At the low concentration, intra-molecular ligation is favored, generating DNA circles. The restriction enzymes BamH I, EcoR I, Hind III, and Sac I are selected because they each recognize a six base pair sequence; therefore, the average fragment size generated upon digestion is 4 kb which can be easily amplified by long range polymerase enzymes. Moreover, according to the sequence previously obtained, there is a BamH I site near the 5' extremity of the intron between exons 19 and 20; thus, if genomic DNA is digested with BamH I, circularized, and amplified with primers designed from sequences downstream of the BamH I site, the resulting fragment contains the sequences from the BamH I site into the intron next to the next BamH I site downstream (FIG. 4). There is no recognition site for the three other restriction enzymes in the sequence previously obtained; thus, the amplification products contain sequences upstream of the known sequence up to the first recognition site encountered and sequences downstream of the known sequences next to the restriction site encountered.

The primers of SEQ ID NOS: 4 and 5 (nucleotides 1184 to 1204; and 1070 to 1090 of SEQ ID NO: 3, respectively) are used for amplification of DNA digested with the enzymes mentioned above. The primers of SEQ ID NOS: 6 and 7 (nucleotides 1413–1434; and 375–394 of SEQ ID NO: 3) are then used on aliquots of the first reaction as templates. These primers are designed to amplify fragments internal to those amplified by primers of SEQ ID NOS: 4 and 5 and this nested reaction confirms that sequences amplified in the first reactions contain EGF sequences. Amplification of DNA digested with Sac I produces a single band of approximately 7,500 bp on an agarose gel and the nested amplification of that material produces a very intense band of smaller size as expected. This product is then cloned and sequenced (SEQ ID NO: 8; Example 3). The DNA fragment has significant homology with EGF sequences from other species as indicated by searches of DNA and protein databases for similarities using version 2.0 of the BLAST algorithm (Altschul et al., 1997). The fragment encompasses 483 nucleotides of intron, exon 19, the 1,320 base pair intron identified previously, exon 20, a 4.8 kilobase intron and 158 nucleotides of exon 21. This fragment thus contains sequences homologous to those identified previously, plus additional sequences, including those encoding the rest of the bovine mature EGF protein.

Human is the only species for which genomic sequences (including introns) of the EGF gene from exons 19 to 21 are available, and included in a 127 kb clone derived from human chromosome 4 (Stone et al., 1998; Genbank accession number AC004050). Exon 19 is 124 base pairs in bovine and human; and exon 20 is 145 base pairs in bovine and 149 base pairs in human. Since the bovine clone of the present invention does not contain the full sequence of exon 21, its size can not be compared with the human exon 21. There is more variation in the sizes of introns, in that the intron between exon 19 and 20 is 1362 base pairs in human and 1320 base pairs in bovine. The intron between exons 20 and 21 is 4799 base pairs in human and 5171 base pairs in bovine. There appears to be insertion of a SINE sequence in the bovine intron; however, the rest of the intronic sequence shows significant homology to the human intron.

FIG. 1 shows the alignment of the bovine with human, porcine, and murine EGF sequences. The overall homologies between the bovine and human, porcine, and murine nucleic acid sequences are 70%, 73%, and 64% respectively, using version 2.0 of the BLAST algorithm to compare the sequences in pairs. The levels of homology vary among the different regions of the sequences; for example, when only the nucleic acid sequences of the mature proteins (FIG. 2) are compared, the homology between bovine (SEQ ID NO: 9) and human, porcine, and murine sequences are 64%, 66%, and 59%, respectively. However, when only the nucleic acid sequences upstream of the sequences encoding the mature proteins are compared, the homology between bovine and human, porcine, and murine sequences are 82%, 85%, and 72% respectively.

The exonic sequences of the bEGF gene obtained above encode the deduced protein of SEQ ID NO: 10. The alignment of the deduced bEGF protein sequence with the human, porcine and murine EGF sequences is shown in FIG. 3. The overall homology between the bovine and human, porcine, and murine deduced protein sequences is 49%, 51%, and 46% when the sequences are compared in pairs using version 2 of the BLAST algorithm. When amino acids with similar characteristics (or from the same group) are considered, the homology is 66%, 69% and 62% with human, porcine and murine respectively. As was the case with the nucleic acid sequence, the levels of homology vary among the different regions of the sequence; for example, when only the mature proteins are compared (SEQ ID NO: 11 for the bovine sequence; FIG. 4), the homology between bovine and human, porcine, and murine protein sequences are 39%, 36% and 36% respectively (65%, 62% and 60% when similar amino acids are considered). However, when only the sequences upstream of the mature proteins are compared, the homology between bovine and human, porcine, and murine are 66%, 73% and 61% respectively (78%, 84% and 73% when similar amino acids are considered).

The deduced mature bEGF protein has a calculated molecular weight of 6112.10 Da, and contains specific amino acids which appear significant for protein structure in other species, namely the glycine in positions 17, 36, and 39 (positions 18, 36, and 39 in other species) and tyrosine 37. In human EGF, tyrosines 13, 22, and 29 are in close proximity to each other (Cooke et al., 1987). In the deduced bEGF protein, tyrosine 13 and 22 are present, as well as phenylalanine 29 which is also an aromatic amino acid, and 5 cysteines as opposed to 6 in other known EGFs. Disulfide bonds in a protein are not a primary reason for the peculiar folding of a protein chain, but rather a device for increasing the stability of an already stable conformation (Watson et al., 1985). The deduced bEGF protein is also a homologue of mouse EGF, as demonstrated by fold recognition indicated by a consensus score of 44.8. Scores greater than 12 are correctly predicted more than 80% of the time (Fisher, 2000).

Analysis of the sequence of SEQ ID NO: 8 reveals an in-frame TGA codon in exon 19 (upstream of the mature region). One of the three chain terminating codons of the genetic code, TGA can also code for selenocysteine, the twenty-first amino acid (Nasim et al., 2000; Tate et al., 1999). In EGF genes from other species, the corresponding codon is TGC which encodes for cysteine; thus, the presence of a selenocysteine would constitute a conservative substitution. In the present invention, Southern blot analysis of bovine genomic DNA is performed to determine the number of copies of the EGF gene in the bovine genome (Example 4). If only one copy appears to be present, it is reasonable to assume that the sequence obtained is from the functional EGF gene and the precursor protein would be a selenoprotein. Bovine genomic DNA is digested in separate reactions with the restriction enzymes BamH I, EcoR I, Hind III, Sac I and Xba I. Thirty-five μg of each digest are run on separate lanes of an agarose gel. The DNA is transferred to a nylon membrane which is hybridized with the fragment of SEQ ID NO: 3 labelled with $^{32}$P-dCTP, washed, and exposed to X-ray film for three days. The probe hybridizes to a single band for each of the digests, strongly suggesting that there is only a single copy of the EGF gene in the bovine genome.

Therefore, one aspect of the present invention is an isolated, purified, or enriched nucleic acid comprising the sequence of SEQ ID NO: 9 and the sequences complementary thereto. The isolated, purified, or enriched nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated, purified or enriched nucleic acids may comprise RNA.

Genomic DNA comprising the sequence of SEQ ID NO: 9 can be isolated using several methods, such as by inverse PCR of bovine genomic DNA digested with Sac I with primers of SEQ ID NOS: 4 and 5, and primers of SEQ ID NOS: 6 and 7 as described. Other primer combinations can also be designed based on the bovine sequence to isolate DNA of SEQ ID NO: 9 by inverse PCR of genomic DNA digested with Sac I or other restriction enzymes. Genomic sequences of SEQ ID NO: 9 may also be obtained by conventional PCR by using, for example, primers of SEQ ID NOS: 6 and 14 as forward and reverse primers, respectively.

Secondly, genomic DNA comprising sequence of SEQ ID NO: 9 may also be isolated by amplifying sequences from exons 20 and 21 by conventional PCR in separate reactions; for example, exon 20 is amplified using the primers of SEQ ID NOS: 6 and 12 as forward and reverse primers, respectively. Exon 21 is amplified using the primers of SEQ ID NOS: 13 and 14 as forward and reverse primers, respectively, with the two resulting fragments being ligated.

Thirdly, genomic DNA comprising the sequence of SEQ ID NO: 9 may also be isolated by contacting a genomic library with a probe made of a fragment of the sequence of SEQ ID NO: 8 under conditions which allow the probe to hybridize specifically to related sequences. Hybridization of the probe to nucleic acids of related sequences may be detected by labelling the probe with a radioactive isotope, a fluorescent dye, or an enzyme capable of catalyzing the formation of a detectable product. Procedures for screening genomic libraries have been described by Ausubel et al (1990) and Sambrook et al. (1989).

The complementary DNA encoding bEGF may be isolated by reverse transcription-PCR. In the present invention, cDNA fragments encoding the mature bEGF protein plus sequences upstream and downstream, are isolated to confirm that the obtained genomic sequences are transcribed (Example 5). Bovine kidney mRNA is reverse transcribed with the primer of SEQ ID NO: 14. Following reverse transcription, cDNA is used in a PCR reaction with the primers of SEQ ID NOS: 16 and 14 as forward and reverse primers, respectively. Several products are observed on agarose gel. A band of slightly more than 400 base pairs is cut out of the gel, purified, and the DNA is used as a template for two separate PCR reactions, namely one with the primers of SEQ ID NOS: 16 and 12 as forward and reverse primers, respectively; and the other with the primers of SEQ ID NOS: 15 and 14 as forward and reverse primers, respectively. The obtained fragments are cloned and sequenced. The combined sequence (SEQ ID NO: 17) is found to be 98% homologous to the corresponding genomic sequences. The differences (6 out of 411 nucleotides) could be due to the fact that tissues from different animals are used to isolate genomic DNA and RNA. When compared to the deduced protein from genomic sequence, two amino acid changes in the mature protein sequence deduced from the cDNA sequence are evident, namely glutamine instead of arginine in position 18, and glutamine instead of histidine in position 32.

Alternatively, complementary DNA sequences encoding bEGF may also be isolated by screening a cDNA library, which is constructed from a bovine tissue expressing the EGF gene. The cDNA library is then contacted with a probe comprising the coding sequence of EGF or a fragment of the coding sequence of EGF under conditions which allow the probe to hybridize specifically to complementary sequences. Complementary DNA which hybridize to the probe are then detected and isolated. Bovine tissues expressing EGF are then identified by Northern blot or PCR analyses.

The sequence encoding the mature bEGF protein (SEQ ID NO: 9) may be synthetically produced by conventional DNA synthesizers, whereby fragments or portions of SEQ ID NO: 9 may be used as intermediates for producing the corresponding full-length sequence. The isolated, purified, or enriched nucleic acids of SEQ ID NO: 9 may thus be used to prepare the peptide of SEQ ID NO: 11.

It is well-known that often, less than a full-length protein has the function of the complete protein. A truncated protein, lacking a N-terminal, internal, or a C-terminal portion may retain full or partial biological and/or enzymatic activity of the full-length protein; for example, human EGF, lacking the last five amino acids on the COOH end, retains its capacity to inhibit gastric acid secretion, while rat EGF, missing up to three N-terminal residues, has identical activity to the native protein (Hollenberg and Gregory 1980; Simpson et al., 1985). Hence, fragments of SEQ ID NO: 9 encoding internally-deleted and truncated bEGF proteins which retain activity of the complete bEGF protein are within the scope of the present invention. Methods for making truncated proteins and proteins with internal deletions are known in the art. The activity of a truncated or internally-deleted bEGF may be verified using for example, a DNA synthesis/cell proliferation assay.

Another aspect of the present invention is an isolated, purified, or enriched nucleic acid which encodes the bEGF protein or fragments comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids of the mature bEGF protein. The coding sequences of these nucleic acids may be identical to the coding sequence of the bEGF protein, or different coding sequences which encode the bEGF protein or fragments comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids of the bEGF protein as a result of the redundancy or degeneracy of the genetic code, which is known to those in the art (Lewin, 1997).

The isolated, purified, or enriched nucleic acid which encodes the mature bEGF protein may include, but is not limited to, only the coding sequence of the mature bEGF protein; the coding sequence of the mature bEGF protein and additional coding sequences, such as leader sequence or precursor protein sequences; or the coding sequence of the mature bEGF protein and non-coding sequences, such as introns or non-coding sequences 5' and/or 3' of the coding sequence.

Alternatively, the nucleic acid sequences of bEGF may be mutagenized using site directed mutagenesis, or other known techniques (Ausubel et al., 1990), to introduce silent changes into the mature bEGF protein, namely changes which do not alter the amino acid sequence encoded by the polynucleotide. Such changes may be desirable in order to introduce codons which are preferred by the host organism, thereby increasing the level of the polypeptide produced by the host cells which contain a vector encoding such a polypeptide.

Certain amino acid substitutions can be made in protein sequences without affecting the function of the protein. The present invention thus relates also to polynucleotides having nucleotide changes which result in amino acid substitutions, additions, deletions, fusions, and truncation in the mature bEGF protein. Such nucleotide changes may be introduced using site directed mutagenesis, random chemical mutagenesis, exonuclease III deletion, and other recombinant DNA techniques (Ausubel et al., 1990). Resulting variants may exhibit the biological properties of bEGF; for example, substituting tyrosine with phenylalanine at position 13 has little effect on the binding of human EGF to its receptor (Tadaki and Niyogi, 1993). Alternatively, such nucleotide changes may be naturally occurring allelic variants, which may be isolated by identifying nucleic acids of bovine origin which specifically hybridize to probes comprising at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120, more preferably at least 130, more preferably at least 140, more preferably at least 150, and most preferably at least 159 consecutive bases of SEQ ID NO: 9 or the sequences complementary thereto.

Hybridization may be conducted under low, moderate, or high stringency conditions. Briefly, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/ml polyriboadenylic acid. Approximately $2\times10^7$ cpm (specific activity $4-9\times10^8$ cpm/µg) of $^{32}P$ end-labelled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm–10° C. for an oligonucleotide probe. The membrane is then exposed to autoradiographic film to detect hybridization signals.

By varying the stringency of the hybridization conditions, nucleic acids having different levels of homology to the probe can be identified and isolated. Stringency may be varied by conducting the hybridization at varying temperatures below the melting temperature (Tm) of the probe, which may be calculated using the following formulas:

For probes greater than 100 nucleotides in length, Tm is calculated using the formula: $Tm=81.5-16.6(\log[Na^+])+0.41(\% \text{ G+C})-(600/N)$ where N is the length of the probe. If the hybridization is carried out in a solution containing formamide, Tm may be calculated using the equation $Tm=81.5-16.6(\log[Na^+])+0.41(\text{fraction G+C})-0.63(\% \text{ formamide})-(600/N)$ where N is the length of the probe.

Prehybridization may be carried in 6×SSC, 5× Denhardt's reagent, 0.5% SDS, 100 µg/ml denatured fragmented salmon sperm DNA; or 6×SSC, 5× Denhardt's reagent, 0.5% SDS, 100 µg/ml denatured fragmented salmon sperm DNA, 50% formamide. Formulas for SSC and Denhardt's solution are listed in Sambrook et al. (1989).

Hybridization is conducted by adding the detectable probe to the above prehybridization solutions. When the probe comprises double stranded DNA, it is denatured before addition to the prehybridization solution. The membrane is contacted with the hybridization solution for a sufficient period of time to allow the probe to hybridize to cDNAs or genomic DNAs containing complementary or homologous sequences. For probes over 200 nucleotides in length, the hybridization may be carried out at 15–25° C. below the Tm. For shorter probes such as oligonucleotide probes, the hybridization may be carried out at 5–10° C. below the Tm. Preferably, for hybridization in 6×SSC, the hybridization is conducted at approximately 68° C. Preferably, for hybridization in 50% formamide-containing solutions, hybridization is conducted at approximately 42° C. All of the foregoing hybridization conditions are considered to be of high stringency.

Following hybridization, the membrane is first washed in 2×SSC, 0.1% SDS at room temperature for 15 minutes; then with 0.1×SSC, 0.5% SDS at room temperature for 30 minutes to 1 hour; then in 0.1×SSC, 0.5% SDS at the hybridization temperature; and finally with 0.1×SSC at room temperature. For oligonucleotide probes, shorter washes are recommended. Nucleic acids which have hybridized to the probe are identified by autoradiography or other conventional techniques.

To obtain nucleic acids of decreasing homology to the detectable probe, less stringent conditions may be used; for instance, the hybridization temperature may be decreased in increments of 5° C. from 68° C. to 42° C. in a hybridization buffer having a $Na^+$ concentration of approximately 1 M. Following hybridization, the membrane may be washed with 2×SSC, 0.5% SDS at the temperature of hybridization. Such conditions are considered to be of "moderate" stringency above 50° C. and "low" stringency below 50° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the membrane may be washed with 6×SSC, 0.5% SDS at 50° C. Such conditions are considered to be of "moderate" stringency above 25% formamide and "low" stringency below 25% formamide.

Such methods may thus be used to isolate nucleic acids having a sequence with at least 75%, at least 80%, at least 85%, at least 90%, at least 95%, or at least 99% homology to the bEGF sequence or fragments comprising at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120, more preferably at least 130, more preferably at least 140, more preferably at least 150, and most preferably at least 159 consecutive bases thereof, and the sequences complementary thereto. Homology may be measured using BLASTN version 2 with the default parameters (Altschul et al., 1990). Additionally, the procedures discussed may be used to isolate nucleic acids which encode polypeptides having at least 55%, at least 60%, at least 65%, at least 70%, at least 75%, at least 80%, at least 85%, at least 90%, at least 95% or at least 99% homology to the bEGF protein or fragments of the bEGF protein comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof as determined by using BLASTX version 2.

The isolated, purified, or enriched nucleic acid of SEQ ID NO: 9, the sequences complementary thereto, or a fragment comprising at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120, more preferably at least 130, more preferably at least 140, more preferably at least 150, and most preferably at least 159 consecutive bases of SEQ ID NO: 9 or the sequences complementary thereto may be used as probes to identify and isolate cDNAs encoding the polypeptide of SEQ ID NO: 11 or variants thereof. In such a procedure, a cDNA library is constructed from RNA extracted from a bovine tissue expressing the bEGF gene, and contacted with a probe comprised of coding sequence under conditions which permit hybridization of the probe to complementary sequences, which are then detected and isolated. By varying the stringency of the hybridization conditions used to identify the EGF cDNA, nucleic acids having different levels of homology to the probe can be identified and isolated. Variant cDNAs may also be isolated by using primers designed from the coding sequence or a fragment thereof in a PCR reaction with cDNA synthesized from bovine RNA as template.

Another aspect of the present invention is the isolated or purified bEGF protein or fragments comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof. The bEGF protein or fragments thereof may be obtained by expression of bEGF DNA sequences in a recombinant host as described herein.

Alternatively, the bEGF protein or fragments comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof can be synthetically produced by conventional peptide synthesizers. Such fragments may serve as intermediates for producing the corresponding full-length bEGF protein by peptide synthesis.

Alternatively, the bEGF protein or fragments thereof may also be obtained using mRNAs transcribed from a DNA construct comprising a promoter linked to the nucleic acid encoding the bEGF protein or fragment thereof. The DNA construct may be linearized prior to conducting an in vitro transcription reaction. The transcribed mRNA is then incubated with an appropriate cell-free translation extract, such as a rabbit reticulocyte extract, to produce the bEGF protein or fragment thereof.

Further, the bEGF polypeptide or fragments thereof may be obtained through biochemical enrichment or purification procedures. The sequence of potentially homologous polypeptides or fragments may be determined by proteolytic digestion and/or microsequencing. The sequence of the prospective homologous polypeptides or fragments can be compared to the deduced bEGF protein or a fragment comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof using a program such as BLASTP, Version 2.

The present invention also extends to variants (including derivatives or analogs) of the bEGF protein or fragments comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof. Such variants may differ in amino acid sequence from the bEGF protein by one or more substitutions, additions, deletions, fusions, and truncations, which may be present in any combination.

The variants may be naturally occurring or created in vitro using site directed mutagenesis, random chemical mutagenesis, Exonuclease III deletion procedures, and standard cloning techniques. Alternatively, such variants, fragments, analogs or derivatives may be created using chemical synthesis or modification procedures.

The variants of the bEGF protein may be variants in which one or more of the amino acid residues of the bEGF protein are substituted with a conserved or non-conserved amino acid residue (preferably a conserved amino acid residue) and such substituted amino acid residue may or may not be one encoded by the genetic code. Conservative substitutions involve substitution of a given amino acid in a polypeptide by another amino acid with similar characteristics, with typical substitutions as follows:

replacement of an aliphatic amino acid such alanine, valine, leucine, and isoleucine with another aliphatic amino acid;

replacement of serine with threonine or vice versa;

replacement of an acidic residue, such as aspartate or glutamate, with another acidic residue; replacement of a residue bearing an amide group, such as asparagine or glutamine, with another residue bearing an amide group;

exchange of a basic residue, such as lysine or arginine, with another basic residue; and replacement of an aromatic residue, such as phenylalanine or tyrosine, with another aromatic residue.

Other variants are those in which one or more of the amino acid residues of the bovine EGF protein include a substituent group.

Still other variants are those in which additional amino acids are fused to the polypeptide such a leader sequence, a secretory sequence, or a sequence that facilitates purification, enrichment, or stabilization of the protein.

In some embodiments, the fragment, derivative, or analog includes precursor sequences, such that the fragment, derivative, or analog can be activated by cleavage of the precursor portion to produce an active peptide.

Another aspect of the present invention are polypeptides or fragments thereof which have at least 55%, at least 60%, at least 65%, at least 70%, at least 75%, at least 80%, at least 85%, at least 90%, at least 95% or at least 99% homology to the bEGF protein or a fragment comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof. Homology may be determined using a program, such as BLASTP version 2 with the default parameters, which aligns the polypeptides or fragments being compared and determines the extent of homology between them. It will be appreciated that amino acid "homology" includes conservative amino acid substitutions as previously described. The polypeptides or fragments having homology to the bEGF protein or a fragment thereof may be obtained by isolating the nucleic acids encoding them using the techniques discussed herein.

The bEGF protein or fragments comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof, may also be used to generate antibodies which bind specifically to the protein or fragment. To detect EGF in a tissue or fluid sample, the sample is contacted with such an antibody, and its ability to bind is then determined by labelling the antibody with either a detectable fluorescent, enzymatic, or radioisotope label, or alternatively, a secondary antibody having such a label. Known assays useful for detection of bEGF in a sample include ELISA, sandwich assay, radioimmunoassay, and Western blot.

Polyclonal antibodies generated against the bEGF protein or fragments comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof may be obtained by direct injection or administration of the protein or fragments to an animal. The antibody obtained then binds the protein itself; thus, even a sequence encoding only a fragment of the protein may be used to generate antibodies which may bind to the full-length native protein. Such antibodies may then be used to isolate the protein from cells expressing it.

For the preparation of monoclonal antibodies, any method which provides antibodies produced by continuous cell line cultures may be used, such as the hybridoma, trioma, human B-cell hybridoma, and the EBV-hybridoma techniques.

Antibodies generated against the bEGF protein or fragments comprising at least 7, more preferably at least 10, more preferably at least 15, more preferably at least 20, more preferably at least 25, more preferably at least 30, more preferably at least 35, more preferably at least 40, more preferably at least 45, more preferably at least 50, more preferably at least 51, and most preferably at least 52 consecutive amino acids thereof may thus be used to detect EGF protein in bovine tissues and fluid, and in screening for a similar protein from other organisms, preferably ruminants. Extracted from bovine or other ruminant tissues or fluid, proteins are contacted with the antibody and those which specifically bind are detected by any of the previously described procedures.

The bEGF gene of the present invention may be used in heterologous hybridization and PCR experiments which enable isolation of EGF encoding genes from other mammals.

II. Overexpression of bEGF Protein

The characterized bEGF coding sequence may be introduced in a variety of expression systems for commercial production. Recombinant DNA technology has facilitated efficient production of peptide hormones such as EGF. Industrial strains of microorganisms (e.g. *Aspergillus niger, Aspergillusficuum, Aspergillus awamori, Aspergillus oryzae,* *Trichoderma reesei, Mucor miehei, Kluyverromyces lactic, Pichia pastoris, Saccharomyces cerevisiae, Escherichia coli, Bacillus subtilis* or *licheniformis*) or plant hosts (e.g. canola, soybean, corn, potato) may be used to produce bEGF. All systems employ a similar approach, whereby an expression construct is assembled to include the protein coding sequence of interest and control sequences such as promoters, enhancers, and terminators, with signal sequences and selectable markers included if desired.

To achieve extracellular expression of bEGF, the expression construct of the present invention utilizes a secretory signal sequence, which is not to be included if cytoplasmic expression is desired. The promoter and signal sequence are functional in the host cell and provide for expression and secretion of the coding sequence product. Transcriptional terminators are included to ensure efficient transcription. Ancillary sequences enhancing expression or protein purification may also be included in the expression construct.

Bovine EGF may be expressed in *E. coli* and *P. pastoris* (Example 6). A DNA fragment containing only the sequence encoding the mature protein is prepared by amplifying the sequences encoding the mature protein on each side of the 5 kb intron separately with primers of SEQ ID NOS: 6 and 12; and primers of SEQ ID NOS: 13 and 14, and then linking the two products with a junction primer (SEQ ID NO: 15). The final product is cloned into *E. coli* and *P. pastoris* expression vectors.

A suitable vector should be able to replicate autonomously in a host cell and accept foreign DNA. A vector carries its own origin of replication, one or more unique recognition sites for restriction endonucleases which can be used for the insertion of foreign DNA, and often recognition sequences (e.g. promoter) for the expression of the inserted DNA. A selectable marker may also be included to allow selection of bacterial cells bearing the desired construct; for example, suitable prokaryotic selectable markers include those that confer resistance to antibiotics such as ampicillin. Any suitable vectors known to those skilled in the art may be selected. Common vectors include, but are not limited to, phage, cosmid, baculovirus, retroviral, and plasmid vectors. The following plasmid vectors are provided by way of example: pEQ40, or a plasmid of the pET series, such as pET26. However, any plasmid vector may be used as long as it is replicable and viable in the host.

Once an appropriate vector has been assembled, a variety of techniques are available for introducing foreign DNA into host cells. The vector or expression construct may be introduced into *E. coli* by electroporation, and into *P. pastoris* cells by protoplast transformation or electroporation. For electroporation, cells are washed with sterile water and resuspended in a low conductivity solution (e.g. 1 M sorbitol solution). A high voltage shock applied to the cell suspension creates transient pores in the cell membranes through which the transforming DNA enters the cells. In *P. pastoris*, the expression construct is stably maintained by integration, through homologous recombination, into the aox1 (alcohol oxidase) locus. Host cells carrying the vector or the expression construct are identified through the use of the selectable marker carried by the expression construct or vector, and the presence of the gene of interest confirmed by hybridization, PCR, antibodies, or other techniques. The transformed microbial cells may be grown by such techniques as batch and continuous fermentation on liquid or semi-solid media. Transformed cells are propagated under conditions optimized for maximal product-to-cost ratios. Product yields may be increased by manipulation of cultivation parameters such as temperature, pH, aeration, and media composition. Careful manipulation and monitoring of the growth conditions for recombinant hyper-expressing *E. coli* cells may result in culture biomass and protein yields of 150 g (wet weight) of cells/l and 5 g of insoluble protein/l, respectively. Low concentrations of a protease inhibitor (e.g., phenylmethylsulfonyl fluoride or pepstatin) may be employed to reduce proteolysis of the over-expressed protein, while protease deficient host cells may be alternatively used to reduce or eliminate protein degradation. For microbial expression, the production of a fusion protein may also be desired to facilitate purification or to protect bEGF from proteolytic degradation.

Following fermentation, the microbial cells may be removed from the medium through down-stream processes such as centrifugation and filtration. If the desired product is secreted, it may be extracted from the nutrient medium. In the case of intracellular production, the cells are harvested and the product released by rupturing cells using mechanical forces, ultrasound, enzymes, chemicals and/or high pressure. Production of an insoluble product, which occurs in hyper-expressing *E. coli* systems, may facilitate product purification. The product inclusions are extracted from disrupted cells by centrifugation, with contaminating proteins removed by washing with a buffer containing low concentrations of a denaturant (e.g. 0.5 to 6 M urea, 0.1 to 1% SDS, or 0.5 to 4.0 M guanidine-HCl). The washed inclusions are solubilized in solutions containing 6 to 8 M urea, 1 to 2% SDS, or 4 to 6 M guanidine-HCl, and solubilized product can be renatured by slowly removing denaturing agents during dialysis.

Bovine EGF may also be expressed in plant cells, such as potato or *Brassica napus*. The expression construct is inserted onto a binary vector capable of replication in *A. tumefaciens* and mobilization into plant cells. The resulting construct is transformed into *A. tumefaciens* cells, and the expression construct is then transferred into *B. napus* leaf cells by conjugal mobilization of the binary vector::expression construct. The expression construct integrates at random into the plant cell genome.

After selection and screening, transformed plant cells can be regenerated into whole plants and varietal lines of transgenic plants developed and cultivated using known methods. Bovine EGF may be extracted from harvested portions or whole plants by grinding, homogenization, and/or chemical treatment. Seed specific lipophilic oleosin fusions facilitate purification by partitioning the oleosin fusion protein in the oil fraction of crushed canola seeds, away from the aqueous proteins (van Rooijen and Moloney, 1994).

If necessary, purification of the product from microbial, fermentation, and plant extracts may be conducted using precipitation (e.g., ammonium sulfate precipitation); chromatography (e.g., gel filtration, ion exchange, affinity liquid chromatography); ultrafiltration; electrophoresis; solvent-solvent extraction (e.g., acetone precipitation); or combinations of such methods.

III. Activity of bEGF Proteins

The obtained recombinant bEGF proteins may be tested for activity using for example, a DNA synthesis/cell proliferation assay, since EGF is a mitogen for numerous types of cells (Example 7). Briefly, bovine fibroblasts are grown to semi-confluence in 24-well plates, to which recombinant bEGF (in various concentrations) and human EGF (the positive control) are then added to separate wells. Eighteen hours after the addition of bEGF, tritiated thymidine is added to each well to be incorporated into the newly synthesized DNA. Eight hours later, the cells are harvested, and the non-incorporated and incorporated thymidine are separated by acid precipitation. The amount of radioactivity in each fraction is determined by scintillation counting. An increase in incorporated tritiated thymidine compared to control cells indicates stimulation of DNA synthesis in fibroblast cells by the recombinant bEGF. With this assay, it is also possible to compare the potencies of human and bEGF to stimulate DNA synthesis and proliferation in bovine cells. In a similar assay, cells are harvested eighteen hours after the addition of bEGF and counted for a determination of bEGF's effect on cell proliferation.

IV. Formulations and Applications of bEGF

The bEGF protein or functionally equivalent fragments thereof; all or a portion of the transformed microbial cultures and plants; and extracts obtained from the cultures or plants can be used directly in applications requiring bEGF activity. Such applications include promotion of growth; prevention or treatment of intestinal infections; increase in nutrient absorption; and acceleration of development of immature gut cells.

The majority of farm animals differ from humans in being unable to take up immunoglobulins across the placenta and instead acquire immunity from uptake of antibodies in the mother's milk through a "leaky," immature gut cell structure. Although this uptake is achieved quite rapidly after birth, the time for replacement of the immature with mature gut cells can be lengthy; for example, as long as four weeks in the piglet and perhaps up to three months in the calf. This stage can create various problems in animal husbandry, particularly preventing the utilization of adult-type diets, making the neonatal animal dependent upon suckling for essential nutrients.

International Publication No. WO 88/04180 to Wilson et al. provides a method to promote precocious maturation of digestive enzymes and growth by administering EGF to farm animals. To enhance the growth of dairy or beef calves, the administered EGF could theoretically be derived from any mammalian sources. It was commonly believed that the EGF active sequence was closely conserved among species. However, the bEGF active sequence is significantly different from all other known mammalian EGF sequences, as demonstrated in this invention. Therefore, to promote the growth of dairy or beef calves, it is preferable to use bEGF which may be likely more potent in affecting bovine digestive physiology and avoiding undesirable side effects if EGF from an alternative source were used. Bovine EGF may also be used to promote growth of other farm animal species, preferably ruminants such as goats and sheep.

EGF may be involved in regulating nutrient uptake; for example, in the rodent, EGF increases electrolytes, glucose and proline transport across jejunal brush-border membranes. The bEGF of the present invention may thus also be used for longer time periods than necessary to modify the gut cell structure as previously described. The potential increase in nutrient uptake in response to bEGF would increase feed efficiency and enhance growth.

The gut cells of the young animal must remain in the immature state for a sufficient time to permit the transfer of the mother's immunity. Administration of bEGF may thus be commenced when calves are two, three, or four days old and continued for only two to four days, if the desired effect is to accelerate the maturation of the gut cell structure; or for a longer period such as four to six weeks, if the desired effect is to take advantage of the increase in nutrient uptake mediated by bEGF. The best time for bEGF administration for optimum effect in the calves may have to be determined experimentally. Bovine EGF may be administered in several ways, namely by either implants or the parenteral route at eight hours intervals as suggested in International Publication No. WO88/04180 to Wilson et al. However, oral administration in the animal's feed or drinking water is preferred. Daily EGF administration enhances weight gain in New Zealand white rabbits at a dose of 100 µg/kg body weight for nine days (U.S. Pat. No. 5,753,622 to Buret et al.). For calves, bEGF may be administered orally, with the dose range varying from 10–10,000 µg/kg per day as an example.

Bovine EGF may also be used to prevent or treat intestinal infection. Such infections include, but are not limited to, enteropathogenic *E. coli* infections such as enteric colibacillosis; giardiasis; and scour. Supplementation with EGF improves intestinal functions of piglets infected with rotavirus (Zijlstra et al., 1994). Further, oral EGF administration reduces the rate of enteric infections in rabbits and prevents the reduction in weight gain caused by infection (Buret et al., 1997). U.S. Pat. No. 5,753,622 to Buret et al. discloses a method for treating scour and other pathogenic infections, and for increasing weight gain by oral administration of EGF or by its administration in the feed of animals. For calves, bEGF may be administered orally, with the dose range varying from 10–10,000 µg/kg per day as an example for prevention or treatment of scour or other pathogenic infections.

For the applications above, bEGF can be prepared in the form of crude bEGF, purified bEGF, or as an extract obtained from transformed microorganisms, transformed plant tissue, or culture or nutrient medium in which bEGF may be secreted by transformed microorganisms. Various formulations of bEGF can thus be prepared for administration to young and adult animals (i.e., cattle, poultry, swine, sheep, goats, other monogastric or ruminant livestock) to promote their growth and health. Bovine EGF can be formulated as a solid, liquid, suspension, feed additive, admixture, or feed composition as follows.

i) Solids—Bovine EGF can be formulated as a solid, as a mineral block, salt, granule, pill, pellet or powder. In the form of a powder, bEGF may be sprinkled into feed bunks or mixed with a ration, or pelleted with other feed stuffs through known processes.

ii) Liquids and Suspensions—Bovine EGF can be incorporated into liquids, formulated as solutions or suspensions, by adding lyophilized or powdered bEGF to a suitable liquid. Bovine EGF can be mixed with the animal's drinking water or provided in other liquid forms for consumption. Bovine EGF can be combined with liquid feed, for example colostrum, hospital milk, whole milk and milk replacers, which are types of liquid feed known in the art used to provide nutrition and immunoprotection to calves. Methods of adding active ingredients to liquid feed are well known in the art, see for example U.S. Pat. No. 5,785,990 to Langrehr.

iii) Feed Additive—Bovine EGF can be administered in the form of a feed additive comprising a preparation of lyophilized microorganisms or plant tissues which have been transformed to express bEGF. The feed additive may be included with the animals' regular feed.

iv) Admixture—Incorporation of active ingredients into animal feed is commonly achieved by preparing a premix of the active ingredient, mixing the premix with vitamins and minerals, and then adding the premix or feed additive to the feed. Bovine EGF can be admixed with other active ingredients known to those in the art, for example enzymes, antibiotics, probiotics, or live preparations of bifidobacteria and lactic acid bacteria. The active ingredients, including bEGF alone or in combination with other active ingredients, can be combined with nutrients to provide a premixed supplement. Nutrients include both micronutrients, such as vitamins (e.g., vitamins A, D, B and K, thiamine, riboflavin, etc.), and minerals (e.g., copper, cobalt, magnesium, iodine, iron sulfate, etc.), and macronutrients (e.g., grain, seeds, grasses, fats and oils). The premix may then be added to dry feed ingredients, including cereals (e.g., wheat, oats, barley, and maize), vegetable protein feed, animal protein feed, and milk products (e.g., milk powders and whey powders).

v) Feed Composition—Bovine EGF can be provided in the form of a feed composition comprising a feedstuff in combination or treated with bEGF. Bovine EGF may be mixed with feedstuff in dry form; e.g. as a powder, or as a liquid to be used as a drench or spray for example. Any conventional feedstuff may be used, including cereal grains such as corn, grain, sorghum, wheat, barley, oats, vegetable protein meals, grass, hay, grass silage, and maize silage.

The formulations of bEGF may be stabilized through the addition of other proteins (e.g., gelatin, skim milk powder, etc.) or chemical agents (e.g., glycerol, polyethylene glycol, reducing agents and aldehydes). Pharmaceutically acceptable carriers, diluents, and excipients may also be incorporated into the formulations, e.g., sugars, powdered milk or milk-by-products, and cellulose derivatives. To ensure that the animals consume a sufficient quantity, flavorings may be added to the formulation to provide bEGF in a form which appears palatable and familiar to the animal. Formulations of bEGF may be adapted for young animals during the growing and fattening stage, in containing modified amounts of bEGF than would be required for adult animals.

Bovine EGF may be administered in several ways, namely by either implants or the parenteral route. However, oral administration in the animal's feed or drinking water is convenient. Alternatively, an bEGF gene with a suitable promoter-enhancer sequence may be integrated into an animal genome and selectively expressed in an organ or tissue which would secrete bEGF into the gastrointestinal tract, thereby eliminating the need for supplemental bEGF.

The dosage of bEGF depends upon many factors that are well known to those skilled in the art, for example, the particular form of bEGF; the condition for which bEGF is being used (i.e., promotion of growth or treatment of intestinal infection); the type, age, and weight of the animal. For calves, bEGF may be administered orally, with the dose range varying from 10–10,000 µg/kg per day as an example. Larger dose ranges are required for adult animals.

The examples herein are given by way of illustration and are in no way intended to limit the scope of the present invention. Efforts have been made to ensure the accuracy with respect to numbers used (e.g., temperature, pH, amounts) but the possibility of some experimental variance and deviation should be recognized.

EXAMPLE 1

Genomic DNA Isolation from *Bos taurus*

Genomic DNA was isolated from bovine blood (*Bos taurus*) using a salt extraction method (Miller et al., 1988). Briefly, nucleated cells obtained from anticoagulated blood were resuspended in 3 ml of nuclei lysis buffer (10 mM Tris-HCl, 400 mM NaCl, and 2 mM Na$_2$EDTA, pH 8.2) in 15 ml centrifugation tubes. The lysates were incubated overnight with 200 µl of 10% SDS and 0.5 ml of protease K solution (1 mg protease K in 1% SDS and 2 mM Na$_2$EDTA). After digestion, 1 ml of saturated NaCl (approximately 6 M) was added to each tube which was shaken vigorously for 15 sec, and then centrifuged at 2500 rpm for 15 min. The supernatant was transferred to another 15 ml tube, 2 volumes of absolute ethanol (room temperature) was added, and the tubes were inverted several times until the DNA precipitated. The DNA strands were removed with a pipette and transferred to a microcentrifuge tube containing 300 µl Tris buffer.

EXAMPLE 2

Amplification, Cloning, and Sequencing of the 1.5 kb Fragment of the bEGF Gene i) Primer Design for PCR Amplification of a Genomic bEGF Fragment The following EGF cDNA sequences from mammalian species were analyzed to identify regions of homology:
1) human (Bell et al., 1986; GenBank accession no. X04571);
2) mouse (Gray et al., 1983; GenBank accession no. J00380);
3) rat (Saggi et al., 1992; GenBank accession no. U04842);
4) pig (Kim et al., 2001; GenBank accession no. AF336151); and
5) horse (Stewart et al.; GenBank accession no. S73527).

A highly conserved region located 83 amino acids upstream of the mature EGF protein was identified, and encodes the amino acid sequence "CTNTEGGY" (amino acids 18 to 25 of SEQ ID NO: 32). This sequence was used to design the primer of SEQ ID NO: 1 such that the potential degeneracies were accommodated by mixing nucleotide bases in these positions: 5' GAC ACA/C/G/T TGC/T ACA AAT ACA/C/G/T GAG GG 3' (nucleotides 46 to 68 of SEQ ID NO: 26). The primer of SEQ ID NO: 2 was designed from a very conserved region of the mature protein of sequence "DGYCLHDG" in human EGF (nucleotides 70 to 77 of SEQ ID NO: 32). Potential degeneracies were also accommodated by mixing nucleotide bases in these positions: 5' GAC/T GGG TAG TGC CTC CAC/T GG/AT GG 3' (nucleotides 31 to 53 of SEQ ID NO: 29). Primers were generated in a DNA/RNA synthesizer (Applied Biosystems, 850 Lincoln Centre Drive, Foster City Calif., 94404, USA, model #392).

ii) PCR Amplification and Cloning of the 1.5 kb Genomic bEGF Fragment

Amplification was performed in 50 µl, with 300 ng bovine genomic DNA as template (as isolated in Example 1), 200 µM each of primers of SEQ ID NOS: 1 and 2, 100 µM dNTPs (Roche Molecular Biochemicals, 201 Boulevard Armand-Frappier, Laval, QC H7V 4A2, Canada, catalog #1 581 295), 1.5 U Taq DNA POLYMERASE (Life Technologies, 9800 Medical Center Drive, P.O. Box 6482, Rockville, Md. 20850, USA, catalog #1 0342-053), 1× reaction buffer (supplied with the enzyme) and 1.5 mM $MgCl_2$. After an initial denaturing step of 3.0 minutes at 96° C., the PCR cycle, which was repeated thirty-five times, consisted of: (1) a denaturing step of 30 seconds at 94° C.; (2) an annealing step of 15 seconds at 57° C.; and (3) an extension step for 2 minutes at 72° C.; followed by a final extension step for 5 minutes at 72° C.

Fifteen µl of the PCR reaction was run on a 1% agarose gel, which was then stained with ethidium bromide, and visualized under ultraviolet light. A band of approximately 1.5 kb was cut out of the gel and purified by passage through glasswool. Briefly, a small amount of glasswool was placed in a 0.5 ml tube with a small hole in the bottom. The piece of gel was placed on top of the glasswool and the tube was placed into a 1.5 ml tube. The tubes were centrifuged at 10,000 rpm for 10 minutes. Two µl of the eluent was used as template in a 100 µl PCR reaction (same conditions as above) to generate sufficient template for cloning. All of the amplification reaction was run on a 1% agarose gel, which was then stained with ethidium bromide, and visualized under ultraviolet light. The 1.5 kb band was cut out of the gel and purified with the QIAQUICK gel extraction kit (Qiagen Inc., 28159 Avenue Stanford, Valencia, Calif. 91355, USA, catalog #28704). Approximately 50 ng of DNA was ligated to 12.5 ng of pGEMT-EASY TA cloning vector (Promega Corporation, 2800 Wood Hollow Road, Madison, Wis. 53711-5399, USA, catalog #A1360) with 3 units of T4 DNA ligase (Promega Corporation, catalog #M1801) in a volume of 10 µl for 16 hours at 4° C. Two µl of the ligation mix was transformed into E. coli MAX Efficiency®DH5α™Competent Cells (Life Technologies, catalog #18258-012).

iii) Sequencing of the 1.5 kb Genomic Bovine EGF Fragment

The complete sequence of the 1.5 kb insert (SEQ ID NO: 3) was determined by the following method. Template DNA was extracted from overnight cultures of E. coli (transformed with a plasmid carrying bEGF) with the QIAPREP Spin Miniprep Kit (Qiagen Inc, catalog #27104). Samples were prepared using a BIGDYE TERMINATOR CYCLE SEQUENCING KIT (Applied Biosystems, catalog #403051) for analysis on a DNA sequencing system (Applied Biosystems, model #373A). Overlapping sequences were generated by primer walking. The DNA sequence data was analysed using SEQUENCHER™ software (Gene Codes Corporation, 640 Avis Drive, Suite 300 Ann Arbor, Mich. 48108, catalog #SQA3.1).

EXAMPLE 3

Inverse PCR for Amplification of DNA Sequences i) Primer Design From the Sequence of the 1.5 kb bEGF Fragment for Inverse PCR The primers were designed from the sequence of the 1.5 kb bEGF gene fragment obtained in Example 2. The primers of SEQ ID NOS: 4 (nucleotides 1184 to 1204 of SEQ ID NO: 3) and 5 (nucleotides 1070 to 1090 of SEQ ID NO: 3) were used for the first amplification; and the primers of SEQ ID NOS: 6 (nucleotides 1413 to 1434 of SEQ ID NO: 3) and 7 (nucleotides 375 to 394 of SEQ ID NO: 3) were designed to amplify a fragment internal to the fragment generated with the primers of SEQ ID NOS: 4 and 5.

ii) Template Preparation

The template was prepared by digesting 1 µg of bovine genomic DNA with 40 U of EcoR I, BamH I, Hind III and Sac I (New England BioLabs Inc., 32 Tozer Road, Beverly, Mass. 01915, USA, catalog #s R0101S, R0136S, R0104S, R0156S) in separate 100 µl reactions at 37° C. overnight. After digestion, the enzymes were inactivated by incubation at 80° C. for 10 minutes. The DNA was diluted to a concentration of 1 µg/ml in water, and then incubated with 30 U of T4 DNA ligase (Promega Corporation, catalog #M1801) and 1× ligase buffer in a volume of 1 ml for 16 hours at 16° C. At this low concentration, intramolecular ligation is favored, generating DNA circles. After ligation, the DNA was cleaned with the QIAQUICK PCR purification kit (Qiagen Inc., catalog #28104) and eluted in a final volume of 30 µl of 10 mM Tris. The volume was reduced to 10 µl by evaporation.

iii) Polymerase Chain Reaction

Five µl aliquots of ligated DNA from each digestion (which corresponded to about 300 ng of DNA) were used as template in PCR. The reaction mixtures contained 1×LA PCR BUFFER II (PanVera Corporation, 545 Science Drive, Madison, Wis. 53711 USA, catalog #RR002M), 2.5 mM MgCl$_2$, 1.6 mM dNTPs (Pan Vera Corporation, catalog #RR002M), 0.2 µM primer of SEQ ID NO: 4, 0.2 µM primer of SEQ ID NO: 5, 1.25 U TAKARA LA TAQ POLYMERASE (PanVera Corporation, catalog #RR002M) in water to 25 µl. After an initial denaturing step of 3.0 minutes at 96° C., the PCR cycle, which was repeated thirty-five times, consisted of: (1) a denaturing step of 30 seconds at 94° C.; (2) an annealing step of 15 seconds at 61° C.; and (3) an extension step for 7 minutes at 68° C.; followed by a final extension step for 5 minutes at 72° C. One µl of amplification products were used directly for 30 cycles of double nested amplifications with the primers of SEQ ID NOS: 6 and 7 in the same conditions as described except that the reaction volume was 50 µl.

Fifteen µl of the products from both first and double nested amplifications were run on a 0.7% agarose gel, which was then stained with ethidium bromide, and visualized under ultraviolet light. The products generated from amplification of DNA digested with Sac I were selected for analysis because the first amplification reaction resulted in a single faint band of approximately 7.5 kb, and the nested amplification resulted in greater DNA of slightly smaller size as expected. The product from the nested amplification was cloned and sequenced as described above. The obtained DNA fragment (SEQ ID NO: 8) has significant homology to human EGF (Bell et al., 1986; GenBank accession no. X04571) as indicated by searches of DNA and protein databases for similarities using version 2.0 of the BLAST algorithm (Altschul et al., 1990). The fragment encompasses 483 nucleotides of intron, exon 19, the 1,320 base pair intron identified previously, exon 20, a 5 kb intron, and 158 nucleotides of exon 21; thus, this fragment contains sequences homologous to the sequences previously identified plus additional sequences, including those encoding the rest of the mature bEGF protein.

EXAMPLE 4

Southern Blot to Determine Number of Copies of the EGF Gene in the Bovine Genome i) Transfer of DNA to a Nylon Membrane To determine the number of copies of the EGF gene in the bovine genome, a Southern blot of bovine genomic DNA was hybridized with the fragment of SEQ ID NO: 3. Briefly, 35 µg of bovine genomic DNA was digested overnight with the restriction enzymes BamH I, EcoR I, Hind III, Sac I and Xba I (New England BioLabs Inc., catalog #s R0136S, R0101S, R0104S, R0156S, R0145S) in separate reactions. The digested DNA was separated in a 0.7% agarose gel at 30 V for 16 hours, and the gel was stained. After the gel was photographed, the DNA was depurinated by submersing the gel in 0.2 N HCl for 10 minutes, and then denatured in 1.5 M NaCl/0.5 N NaOH with three 15 minutes washes with gentle shaking. The gel was then neutralized in 1.5 M NaCl/1 M Tris-HCl (pH 7.5) with three 10 minute washes. DNA was then transferred to a positively charged Nylon Membrane (Roche Molecular Biochemicals, catalog #1 417 240) by upward capillarity with 10xSSC as the transfer buffer. After 24 hours, the membrane was placed between blotting paper and baked at 80° C. for 3 hours.

ii) Probe Preparation

Twenty-five ng of the fragment of SEQ ID NO: 3 was labelled with 50 µCi of α$^{32}$PdCTP (Amersham Pharmacia Biotech, 500 Morgan Boulevard, Baie d'Urfe, QC H9X-3V1, Canada, catalog #PB 10205-250 µCi) using a random labelling kit (Roche Molecular Biochemicals, catalog #1 004 760). The probe was purified using the NUC-TRAP column (Stratagene, 11011 North Torrey Pines Road, La Jolla, Calif. 92037, USA, catalog #400 701).

iii) Pre-hybridization, Hybridization, Washes and Autoradiography

The membrane was pre-wetted in 2xSSC for 15 minutes. Pre-hybridization was carried out at 42° C. for 1 hour in a volume of 10 ml of 50% deionized formamide, 1% SDS, 1 M NaCl, 10% dextran sulfate, and 1 mg of denatured salmon sperm DNA in a rotary hybridization oven. The probe was then added to the pre-hybridization buffer and hybridization was carried out for 12 hours at 42° C. The membrane was washed twice in 100 ml of 2xSSC/1% SDS at room temperature for 30 min; twice in 200 ml of 0.2xSSC/0.1% SDS at 60° C. for 1 hour; and twice in 200 ml of 0.1xSSC/0.1% SDS at 60° C. for 30 minutes. The membrane was exposed to KODAK BIO-MAX MS film (Kodak Canada, 3500 Eglinton Avenue West, Toronto, ON M6M 1V3, Canada, catalog #1435726) for three days.

EXAMPLE 5 cDNA Isolation

To confirm that the genomic sequences obtained were transcribed, the corresponding cDNA was cloned. One pg of bovine kidney mRNA (Clontech, 1020 East Meadow Circle, Palo Alto, Calif. 94303-4230, USA, catalog #6824-1) was reverse transcribed with 10 pmol of the primer of SEQ ID NO: 14 in a reaction containing the 1x reverse transcription buffer, 10 mM DTT, 1 mM dNTP mix, 40 U RNAse inhibitor and 15 U of Thermoscript reverse transcriptase (Life Technologies, catalog #11146-024) for 1 hour at 55° C. The reverse transcriptase was inactivated at 85° C. for 5 mm, 100 U RNAse H was added, and the reaction was incubated at 37° C. for 20 minutes and then heated at 70° C. for 10 minutes. The cDNA was cleaned with a QIAQUICK PCR purification kit (Qiager Inc., catalog #28104).

Five µl of the reverse transcription reaction was used as template in a PCR reaction containing 1x PCR buffer (containing 1.5 mM MgCl$_2$), 0.2 mM of each dNTP, 0.4 µM primer of SEQ ID NO: 16, 0.4 µM primer of SEQ ID NO: 14, and 0.625 U TAKARA Taq DNA POLYMERASE (PanVera Corporation, catalog #TAKR001B) and water to 25 µl. After an initial denaturation step at 94° C. for 4 minutes, the PCR cycle, which was repeated fifty times, consisted of: (1) a denaturation step of 30 seconds at 94° C.; (2) an annealing step of 30 seconds at 59° C.; and (3) an extension step for 30 seconds at 72° C.; followed by a final extension step for 10 minutes at 72° C. for 10 minutes.

Fifteen µl was loaded on a 1.8% agarose gel, which was then stained with ethidium bromide, and visualized under ultraviolet light. Several products from the reaction were observed on agarose gel. A band of slightly more than 400 bp was cut out of the gel, purified, and the DNA was used as template for two separate PCR reactions: one with the primers of SEQ ID NOS: 16 and 12 as forward and reverse primers, respectively; and the other with the primers of SEQ ID NOS: 15 and 14 as forward and reverse primers, respectively. The conditions were the same as above except that only 35 cycles were performed. The fragments obtained were cloned and sequenced (SEQ ID NOS: 17 and 18) and the sequences were found to be 98% homologous to the corresponding genomic sequences using version 2 of the BLAST algorithm (Altschul et al., 1997).

EXAMPLE 6

Overexpression of the Bovine EGF Mature Protein in E. coli and P. pastoris i) Amplification of the Sequences Coding for the Mature Bovine EGF Protein Without the Intron To generate the sequence for overexpression of the mature bovine EGF protein, the 5 kb intron that separates this sequence had to be removed. The sequence encoding the N-terminus of the protein was amplified with the primers of SEQ ID NOS: 6 and 12, while the sequence encoding the Carboxy terminus of the protein was amplified with the primers of SEQ ID NOS: 13 and 14 in a separate reaction. Five units of Pfu DNA POLYMERASE (Stratagene, catalog #600153) was used in the presence of 1.5 mM $MgCl_2$ for an initial denaturation step of 4 minutes at 94° C., followed by the PCR cycle, which was repeated thirty times and consisted of: (1) a denaturing step of 30 seconds at 94° C.; (2) an annealing step of 30 seconds at 57° C.; and (3) an extension step of 30 seconds at 72° C.; followed by a final extension step of 10 minutes at 72° C.

The PCR reactions were run on a 1.8% agarose gel, stained with ethidium bromide, and the products were purified using the QIAQUICK Gel Extraction kit (Qiagen Inc., catalog #28704) and 1 µl of each product was used as template for the synthesis of a single strand linking the two fragments. This was accomplished by amplifying with the primers of SEQ ID NOS: 6 and 15 (which overlaps the 3' extremity of the N-terminal fragment and the 5' extremity of the carboxy fragment) in the forward direction. The single stranded product was cleaned with the QIAQUICK PCR Purification kit (Qiagen Inc., catalog #28104) and eluted in 50 µl. One µl of the eluent was used as template for amplification with the primers of SEQ ID NOS: 6 and 14. The 292 bp product was purified from a 1.5% agarose gel and cloned into pGEMT-EASY TA cloning vector (Promega Corporation, catalog #A1360) as described in Example 2.

ii) Construction of the E. coli Expression Vector

A number of E. coli expression vectors are available commercially, and can be used to produce recombinant bEGF. Herein, the construct was prepared with the vector pQE40 (Qiagen Inc., catalog #32915), which is based on the T5 promoter transcription-translation system and is designed for expression of murine dihydrofolate reductase (DHFR)-fusion protein which protects short peptides such as EGF from proteolysis. The lac repressor represses the T5 promoter; however, addition of isopropyl-p-D-thiogalactoside (IPTG) inactivates the lac repressor, subsequently inducing expression of the recombinant protein. The sequences encoding the mature EGF protein and cloned into pGEMT-EASY TA cloning vector (Promega Corporation, catalog #A1360) were amplified with the oligonucleotide primers of SEQ ID NOS: 18 and 19. Such primers were designed to contain suitable restriction sites (Sph I for the primer of SEQ ID NO: 18 and Hind III for the primer of SEQ ID NO: 19) to facilitate cloning of the resulting product into pQE40. The primer of SEQ ID NO: 18 also contained coding sequences for a recognition site for Factor Xa. The amplified product was digested with Sph I and Hind III and ligated into similarly cleaved pQE40.

iii) Transformation of E. coli and Expression of bEGF

The construct pQE40::bEGF is used to transform competent E. coli M15 [pRep4] cells (Qiagen Inc., catalog #34210) by the heat shock method (Sambrook et al., 1989). Cells are then plated on LB-agar containing 25 µg/ml kanamycin and 100 µg/ml ampicillin and grown overnight at 37° C. To identify clones with high levels of expression, single colonies of transformants are picked into 1.5 ml of LB medium with antibiotics as above. These small cultures are grown overnight and are used to inoculate 10 ml of LB medium with antibiotics. These cultures are then grown at 37° C. for 30 minutes with vigorous shaking until the $OD_{600}$ reaches 0.5–0.7. IPTG is added to a final concentration of 1 mM to induce expression of the recombinant protein and the cultures are grown for an additional 4–5 hours. The cells are harvested by centrifugation at 1500 RPM for 10 minutes, resuspended in 400 µl of cell lysis buffer, and purified with Ni-NTA (Qiagen Inc., catalog #30210). The recombinant His-tagged protein is purified with Ni-NTA columns (Qiagen Inc., catalog #30210) and the amount of protein produced is estimated by SDS-PAGE and Western blotting. High expressing clones may thus be used for establishing expression parameters, testing purification protocols, and for producing the recombinant protein on large scale.

iv) Construction of the P. pastoris Expression Vector

Sequences encoding for the mature bovine EGF protein and suitable for insertion into P. pastoris expression vectors were generated by PCR. Two constructs for extracellular expression, designated as "ExtraStop" and "ExtraTag," were prepared. The ExtraStop construct was generated with primer alphaA bEGF forward (SEQ ID NO: 20) and alphaA&ZB bEGF reverse (SEQ ID NO: 21). The ExtraTag construct was generated with the alphaA bEGF forward primer and the alpha AFXa&mycHIS reverse primer (SEQ ID NO: 22). These primers contain recognition sites for restriction enzymes to facilitate cloning of the resulting PCR products into P. pastoris expression vectors (Xho I site in the forward primer and Xba I site in the reverse primers). These primers were used to amplify the mature bovine EGF protein coding sequences prepared as previously described. Ampli-Taq DNA POLYMERASE (Applied Biosystems, 850 Lincoln Centre Drive, Foster City Calif., 94404, USA, catalog #N808-0160) was used in a PCR cycle, which was repeated thirty-five times, consisting of: (1) a denaturation step for 1 minute at 94° C.; (2) an annealing step of 1 minute at 65° C.; and (3) a final extension step of 4 minutes at 72° C.

PCR products were purified from 1.5% agarose gel and cloned into a pGEMT-EASY cloning vector (Promega Corporation, catalog #A1360) for propagation of the construct into E. coli. To transfer the bEGF coding sequence into a P. pastoris expression vector, the constructs were digested out of pGEMT with Xho I and Xba I (New England BioLabs Inc., catalog #s R0146S, R0145S), gel purified, and ligated into a similarly digested pPICZαA vector (Invitrogen Corporation, 3985 B Sorrento Valley Blvd. San Diego, Calif. 92121, USA, catalog #V195-20). The ligated DNA was used to transform competent E. coli MAX Efficiency®DH5α™ Competent Cells (Life Technologies, catalog #18258-012) and the resulting transformants were screened by PCR for the presence of the desired constructs. Plasmid DNA was purified and was used to transform P. pastoris.

v) Transformation of P. pastoris and bEGF Expression

P. pastoris cells are prepared by inoculating 50 ml of fresh YPD medium (50 ml) with 1 to 5 ml of an overnight culture of strain GS115 (Invitrogen Corporation, catalog #K1710-01), and grown at 28° C. with shaking until the culture reaches an $OD_{600}$ of 1.2–1.5 (about 6 hours). Cells from 20 ml of culture with an $OD_{600}$ equal to 1.5 are harvested by centrifugation, washed with 10 mM Tris, 1 mM EDTA, 0.1 M LiCl, and 0.1 M dithiothreitol buffer (pH 7.4), and resuspended in 1 ml of TE/LiCl/DTT buffer. The suspension is incubated at 30° C. for 1 hour; washed once with 1 ml of ice-cold water and once with 1 ml of ice-cold 1 M sorbitol; and resuspended in 160 µl of ice-cold sorbitol to obtain a cell concentration of about $10^{10}$ cells/ml. The expression construct pPICZα::bEGF (5 to 10 μg), previously linearized with BstX I (New England BioLabs Inc., catalog #R0113S), is mixed with 80 μl of cells and placed in chilled electroporation cuvettes (0.2 cm interelectrode distance) on ice for 5 minutes. The cells are pulsed at 1.5 kV, 20 μF, 200 Ω, with a GENE PULSER (Bio-Rad Laboratories, Ltd., 5671 McAdam Road, Mississauga, ON L4Z 1N9, Canada, catalog #165 2105). One ml of ice-cold 1 M sorbitol is then added to the cuvette and the resulting mixture incubated at 30° C. for 1 to 2 hours. Zeocin resistant transformants are selected on YPD agar containing 100 μg/ml zeocin and 1 M sorbitol. Biomass is produced from zeocin resistant clones by growing isolates in BMGY broth at 30° C., 300 rpm for 24 hours. Cells are harvested by centrifugation, resuspended in induction medium (BMMY), and incubated for a further 6 to 12 days, with the addition of absolute methanol to a final concentration of 0.5% every 24 hours. Aliquots of culture are collected and stored at −20° C. until required for analysis.

vi) Purification of Expressed Proteins with Ni-NTA Affinity Resin

Tagged proteins are purified using Ni-NTA agarose (Qiagen Inc., catalog #30210). Nickel ions immobilized on NTA magnetic agarose beads have a high affinity for polyhistidine. The vectors used for cloning the bEGF sequences into *E. coli* and *P. pastoris* encode for 6 consecutive histidine residues (6× tag) at the carboxy terminus of the recombinant protein (at the N-terminus for the *E. coli* vector). A 3 ml aliquot of Ni-NTA resin (a 50% slurry in ethanol) is washed 4 times with 5 volumes (15 ml) of a cell lysis buffer (300 mM NaCl and 10 mM imidazole in 50 mM $NaH_2PO_4$, pH 8.0). The resin is resuspended in 3 ml of cell lysis buffer and the pH adjusted to 8.0 with 0.2 M NaOH. Purified protein is obtained by mixing 1 ml of suspended *E. coli* or *P. pastoris* cells with 100 μl of washed resin. Samples are incubated for 30 minutes at 4° C. with gentle mixing, and then washed twice with 500 μl of a wash buffer (300 mM NaCl and 20 mM imidazole in 50 mM $NaH_2PO_4$, pH 8.0). Purified proteins are eluted from the slurry with 100 ml of an elution buffer (300 mM NaCl, 250 mM imidazole in 50 mM $NaH_2PO$, pH 8.0). The His tag from the bEGF produced in *E. coli* or *P. pastoris* is removed by cleavage with Factor Xa (New England BioLabs Inc., catalog #P8010S) and the bEGF protein is again cleaned with the Ni-NTA affinity resin (only the His tag will bind the resin). The biological activity of the recombinant proteins is tested thereafter in a cell proliferation/DNA synthesis assay.

EXAMPLE 7

Cell Proliferation/DNA Synthesis Assay

Bovine fibroblasts were isolated from skeletal muscle connective tissue, and grown to the desired level of confluence in 1 ml of MEM (Life Technologies, catalog #23700) containing 10% horse serum (HyClone Laboratories, Inc., 1725 S. HyClone Road, Logan, Utah 84321, USA, catalog #SH30074.03) and sodium bicarbonate in 24-well plates. Recombinant bEGF or protein fractions containing bEGF were added to the medium and cells were cultured for 18 hours at 39° C. Recombinant human EGF (Sigma, 3050 Spruce Street, St. Louis, Mo., USA, catalog #E9644) served as a positive control and no addition as a negative control. One μCi/ml of tritiated thymidine (Amersham Pharmacia Biotech, catalog #TRA310-250 μCi) was added to each well and the culture incubated for another 18 hours at 39° C. After removing the medium, the cells were washed twice with 200 μl PBS and then detached with 0.1% trypsin in a volume of 200 μl for about 30 minutes at 39° C. After disrupting cells by passage in and out of pipette tips, 125 μl was removed to count cells with a hemacytometer and to the remainder, 375 μl of cold 20% TCA was added to precipitate for 20 minutes. Cells were then transferred to 1.5 ml centrifuge tubes and each well was washed with 200 μl of PBS which was added to the appropriate tube. The tubes were centrifuged for 15 minutes at 14000 rpm and the supernatant was transferred to a scintillation vial. The pellet was washed with 200 μl of 10% TCA and re-centrifuged. The supernatant was transferred to the same scintillation vial, thus containing the labelled thymidine taken up by the cells but not incorporated into DNA. The pellet was solubilized with 40 μl of 1 N NaOH for 10 minutes and transferred to a scintillation vial containing 75 μl of 1 N HCl, and thus contained labelled thymidine that was incorporated into DNA. Scintillant was added to all vials which were counted for 1 min/sample in a scintillation counter (Beckman Coulter Inc., 4300 N. Harbor Boulevard, P.O. Box 3100, Fullerton, Calif. 92834-3100, USA, model # LS 6001C).

References

Altschul, S. F., Madden, T. L., Schaffer, A. A., Zhang, J., Zhang, Z., Miller, W. and Lipman, D. J. (1997) Gapped BLAST and PSI_BLAST: a new generation of protein database search programs. Nucleic Acids Res. 25: 3389–3402.

Ausubel, F. A., Brent, R, Kingston, R. E., Moore, D. D., Sneidman, J. G., Smith, J. A. and Struhl, K. (eds) (1990) Current Protocols in Molecular Biology. Green Publishing and Wiley-Interscience, New York.

Bell, G. I., Fong, N. M., Stempien, M. M., Wormsted, M. A., Caput, D., Ku, L., Urdea, M. S., Rall, L. B. and Sanchez-Pescador, R. (1986) Human epidermal growth factor precursor: cDNA sequence, expression in vitro and gene organization. Nucleic Acids Res. 14: 8427–8446.

Benkel, B. F. and Fong, Y. (1996) Long range-inverse PCR (LR-IPCR): extending the useful range of inverse PCR. Genetic Analysis: Biomol. Eng. 13: 123–127.

Buret, A., Gall, D. G., Olson, M. E., and Hardin, J. A. (1997) Anti-infective properties of a mucosal cytokine: epidermal growth factor (EGF). Proc. Agric. Biotechnol. Workshop, AARI, P.19.

Carpenter, G. and Cohen, S. (1979) Epidermal growth factor. Ann. Rev. Biochem. 48: 193–216.

Clare, J. J., Romanos, M. A., Rayment, F. B., Rowedder, J. E. Smith, M. A., Payne, M. M., Sreekrishna, K. and Henwood, C. A. (1991) Production of mouse epidermal growth factor in yeast: high-level secretion using *Pichia pastoris* strains containing multiple gene copies. Gene 105: 205–212.

Cooke, R. M., Wilkinson, A. J., Baron, M., Pastore, A., Tappin, M. J., Campbell, I. D., Gregory, H. and Sheard, B. (1987) The solution structure of human epidermal growth factor. Nature 327: 339–341.

Donovan, S. M. and Odle, J. (1994) Growth factors in milk as mediators of infant development. Ann. Rev. Nutr. 14: 147.

Fisher, D. (2000) Hybrid for recognition: combining derived properties with evolutionary information. Pacific Symp. Biocomputing, Hawaii, 119–130, January 2000, World Scientific.

Gray, A., Dull, T. J. and Ullrich, A. (1983) Nucleotide sequence of epidermal growth factor cDNA predicts a 128,000-molecular weight protein precursor. Nature 303: 722–725.

Hollenberg, M. D. and Gregory, H. (1980) Epidermal growth factor-urogastrone: biological activity and receptor binding of derivatives. Mol. Pharmacol. 17: 314–320.

Kim, J. G., Vallet, J. L. and Christenson, R. K. (2001) Characterization of uterine epidermal growth factor during pregnancy in pigs. Domestic Animal Endocrinology 20(4): 253–265.

Lewin, B. (1997) Genes VI, Oxford University Press, Menlo Park, Calif., USA.

Miller, S. A., Dykes, D. D. and Polesky, H. F. (1988) A simple salting out procedure for extracting DNA from human nucleated cells. Nucleic Acids Res. 16: 1215.

Nasim, M. T., Jaenicke, S., Belduz, A., Kollmus, H., Flohe, L. and McCarthy, J. E. (2000) Eukaryotic selenocystein incorporation follows a nonprocessive mechanism that competes with translational termination. J. Biol. Chem. 275: 14846–14852.

Ochman, H., Gerber, A. S. and Hartl, D. L. (1988) Genetic applications of an inverse polymerase chain reaction. Genetics 120: 621–623.

Saggi, S. J., Safirstein, R. and Price, P. M. (1992) Cloning and sequencing of the rat preproepidermal growth factor cDNA: comparison with mouse and human sequences. DNA Cell Biol. 11: 481–487.

Sambrook, J., Fritsch, E. F. and Maniatis, T. (1989) Molecular Cloning. A Laboratory Manual. $2^{nd}$ Edition. Cold Spring Harbor Laboratory Press. Cold Spring Harbor, N.Y.

Shin, S. Y., Watanabe, M., Kako, K., Ohtaki, T. and Munekata, E. (1994) Structure-activity relationship of human epidermal growth factor (h-EGF). Life Science 55: 131–139.

Simpson, R. J., Smith, J. A., Mortiz, R. L., O'Hare, M. J., Rudland, P. S., Morrison, J. R., Lloyd, C. J., Grogo, B., Burgess, A. W. and Nice, E. E. (1985) Rat epidermal growth factor: complete amino acid sequence. Homology with the corresponding murine and human proteins; isolation of a form truncated at both ends with full in vitro biological activity. Eur. J. Biochem. 153: 629–637.

Stewart, F., Powel, C. A., Lennard, S. N., Allen, W. R., Amet, L. and Edwards, R. M. (1994) Identification of the horse epidermal growth factor (EGF) coding sequence and its use in monitoring EGF gene expression in the endometrium of the pregnant mare. J. Mol. Endo. 12: 341–350.

Stone, N. E., Schmutz, J. J., Shang, J., Cox, D. R. and Myers, R. M. Homo sapiens chromosome 4 clone B207D4 map 4q25, complete sequence. Genbank Accession No. AC004050, submitted Jan. 28, 1998.

Tadaki, D. K. and Niyogi, S. K. (1993) The functional importance of hydrophobicity of the tyrosine at position 13 of human epidermal growth factor in receptor binding. J. Biol. Chem. 268: 10114–10119.

Tate, W. P., Mansell, J. B., Mannering, S. A., Irvine, J. H., Major, L. L. and Wilson, D. N. (1999) UGA: a dual signal for 'stop' and for recoding in protein synthesis. [Review]. Biochemistry 64: 1342–1353.

van Rooijen, G. J. H. and Moloney, M. M. (1994) Plant seed oil-bodies as carriers for foreign proteins. Bio/Technology 13: 72–77.

Watson, J. D., Hopkins, N. H., Roberts, J. W., Steitz, J. A. and Weiner, A. M. (1985) Molecular Biology of the Gene. Vol.1. $4^{th}$ ed. The Benjamin/Cummings Publishing Company, Inc. Menlo Park, Calif., USA.

Zijlstra, R. T., Odle, J., Hall, W. F., Petschow, B. W., Gelberg, H. B. and Litov, R. E. (1994) Effect of orally administered epidermal growth factor on intestinal recovery of neonatal pigs infected with rotavirus. J. Ped. Gastroent. Nutr. 19: 382–390.

Patent Documents

Barr, P. J., Merryweather, J. P., Mullenbach, G. T., Urdea, M. S. and Valenzuela, P. Gene for human epidermal growth factor and synthesis and expression thereof. U.S. Pat. No. 5,096,825, issued Mar. 17, 1992.

Buret, A. G., Gall, D., Hardin, J. A. and Olson, M. E. Use of epidermal growth factor as a gastrointestinal therapeutic agent. U.S. Pat. No. 5,753,622, issued May 19, 1998.

Langrehr, J. S. Feed fortifier and enhancer for preruminant calves and method of using same. U.S. Pat. No. 5,785,990, issued Jul. 28, 1998.

Wilson, T. J. G., Tivey, D. R., Smith, M. W., James, P. S. and Peters, T. J. International Publication No. WO 88/04180, published Jun. 16, 1988.

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are, unless otherwise specifically defined herein, used as terms of description and not of limitation. There is no intention, in using such terms and expressions, of excluding equivalents of the features illustrated and described, it being recognized that the scope of the invention is defined and limited only by the claims which follow.

SEQUENCE LISTING

```
<160> NUMBER OF SEQ ID NOS: 37

<210> SEQ ID NO 1
<211> LENGTH: 23
<212> TYPE: DNA
<213> ORGANISM: Artificial Sequence
<220> FEATURE:
<223> OTHER INFORMATION: Description of artificial sequence:
      oligonucleotide useful as primer
<220> FEATURE:
<221> NAME/KEY: misc_feature
<222> LOCATION: (6)..(6)
<223> OTHER INFORMATION: n is a, c, t, or g
<220> FEATURE:
<221> NAME/KEY: misc_feature
```

-continued

```
<222> LOCATION: (18)..(18)
<223> OTHER INFORMATION: n is a, c, t, or g

<400> SEQUENCE: 1
gacacntgya caaatacnga ggg                                          23

<210> SEQ ID NO 2
<211> LENGTH: 23
<212> TYPE: DNA
<213> ORGANISM: Artificial sequence
<220> FEATURE:
<223> OTHER INFORMATION: Description of artificial sequence:
      oligonucleotide useful as primer

<400> SEQUENCE: 2 gayggqtact gcctccaygr tgg                                          23

<210> SEQ ID NO 3
<211> LENGTH: 1456
<212> TYPE: DNA
<213> ORGANISM: Bos taurus
<220> FEATURE:
<221> NAME/KEY: exon
<222> LOCATION: (2)..(56)
<223> OTHER INFORMATION:
<220> FEATURE:
<221> NAME/KEY: Intron
<222> LOCATION: (57)..(1376)
<223> OTHER INFORMATION:
<220> FEATURE:
<221> NAME/KEY: exon
<222> LOCATION: (1377)..(1456)
<223> OTHER INFORMATION:

<400> SEQUENCE: 3
aaaccacact tgcacgtgtg ctggcgactt gtctgagcct ggacagattt gccctggtag     60
gttggtgggt ggtttggatc caaggggagg gacttgattc ccaaaaaatc tctacttaag    120
tgtgttttca ttagagcttc aagaaatcat ttggttcaat caggctggtg agtttcctct    180
cctgattaga ttgatgataa ggtcgagaat gaaatggtcc aagttttctt aatttaatag    240
catctggaat aaatcctttt ttattattca caatgcaata taggtgagaa cacaggtggt    300
tctctttaac tattcagtta atgtcctgat ttgtaatgtt gatttkgggg gccgctggga    360
gaacttggca gggctagaca ggttggggag gatgtctggt ctgctggcat tttgaatcac    420
tttcaaggat tttaaagtat tactttaaaa agtcagtatt tcttgagctg aatgagaact    480
ttttaaattg ttaattatac ccatttctgc ttcctgaaac ctcccctgc aaaagcagta     540 tcttctcacc atcagcactc cagaatgggg aggggtggtc agagggtggc ggggggttgg    600
cttcaaagac accagaagcc agaatcagct tagtcactga cagccattta cccatctcag    660
ccctgcaagc agaaaacatc ctgaaaaagg aaaattcggc acttgtttgg ggctctggtt    720
tttcagtata ttatttctc aaataatttg ctcttcttag aggtattgaa aaactcctaa     780
tacttatgta gtcagctaca caccctaatg tttttctttt aaagagcagc gaaccattaa    840
taaaaaggga cttttccact tgggcatccc ctctgttatg gtaacatttc ctctctgtca    900
aagttgctag tcctgtcttt gagggctccc ctgaaagtta aatgcgttta gaagcaagta    960
tcctgtggga taaattttg agactccagg gaactgggg taattgactg gatagtggtg    1020
ggtggttaca agccatgaag agagacggtt gttcagtgag accctcttaa gctaactgtt   1080
gttttacatg gtgtgttttt atagatgaca gatggctttt ataagagatc tgtactcagg   1140
gttcatatgg tcttaggatt gaccattctc ttacttgcct ccaatatact ttatgtcaaa   1200
```

```
tagtgctgaa cctcaagcaa aatgggtgac tccatagcaa attcataagg tctggttaag      1260
aaagtgaaat tatttgttcca tatgacaaat tgttcacaga aactagttcc tgatgttgat     1320
atctgaaaga ctccagtcac ttcagaaagt aaaagaaatg cctttgattc ttctagactc     1380
tactctgctg tctcaccttg ggaagaatgg acacaatttt ttgaaaaaat gtttccctga     1440 atatacccg aatttt                                                      1456

<210> SEQ ID NO 4
<211> LENGTH: 21
<212> TYPE: DNA
<213> ORGANISM: Bos taurus

<400> SEQUENCE: 4
gaccattctc ttacttgcct c                                                21

<210> SEQ ID NO 5
<211> LENGTH: 21
<212> TYPE: DNA
<213> ORGANISM: Bos taurus

<400> SEQUENCE: 5
agagggtctc actgaacaac c                                                21

<210> SEQ ID NO 6
<211> LENGTH: 22
<212> TYPE: DNA
<213> ORGANISM: Bos taurus

<400> SEQUENCE: 6
tgtctcacct tgggaagaat gg                                               22

<210> SEQ ID NO 7
<211> LENGTH: 20
<212> TYPE: DNA
<213> ORGANISM: Bos taurus

<400> SEQUENCE: 7
ccgctgggag aacttggcag                                                  20

<210> SEQ ID NO 8
<211> LENGTH: 7387
<212> TYPE: DNA
<213> ORGANISM: Bos taurus
<220> FEATURE:
<221> NAME/KEY: Intron
<222> LOCATION: (1)..(485)
<223> OTHER INFORMATION:
<220> FEATURE:
<221> NAME/KEY: CDS
<222> LOCATION: (486)..(609)
<223> OTHER INFORMATION:
<220> FEATURE:
<221> NAME/KEY: Intron
<222> LOCATION: (610)..(1930)
<223> OTHER INFORMATION:
<220> FEATURE:
<221> NAME/KEY: CDS
<222> LOCATION: (1931)..(2075)
<223> OTHER INFORMATION:
<220> FEATURE:
<221> NAME/KEY: Intron
<222> LOCATION: (2076)..(7227)
<223> OTHER INFORMATION:
<220> FEATURE:
<221> NAME/KEY: CDS
<222> LOCATION: (7228)..(7387)
```

-continued

```
<223> OTHER INFORMATION:
<220> FEATURE:
<221> NAME/KEY: mat_peptide
<222> LOCATION: (1981)..()
<223> OTHER INFORMATION:
<220> FEATURE:
<221> NAME/KEY: misc_feature
<222> LOCATION: (537)..()
<223> OTHER INFORMATION: TGN is Xaa, Xaa is probably selenocysteine
<220> FEATURE:
<221> NAME/KEY: misc_feature
<222> LOCATION: (539)..()
<223> OTHER INFORMATION: N is a,  Xaa is probably selenocysteine
<220> FEATURE:
<221> NAME/KEY: misc_feature
<222> LOCATION: (7228)..()
<223> OTHER INFORMATION: mature protein ends at residue 7228

<400> SEQUENCE: 8
cagcgatgga aaattaaaga aggaaggacc taaaggttat ggtggtgata ctaagaaaag      60
aaaaagatgg gtagttggga aagaaagaga tgatttcatt tatatctgtg ttaaaagggc     120
aaaatgtttt atttaatagg atctgaactt ctaaatgttt acctagagat agttwaccat     180
ctccaacttt cccacggagc tatttgtgct gggaagtttc ctttccttcc aagcagtagg     240
gaagcttcca gcctgacatc aggagtttac ctgcatgggt atgcacccca gggacccagt     300
tcatctctct ttccaacatg gataatgaaa ttttgaatc taaaaatgta cagagctctg      360
agaacatgta tcatgacaca aattgaagat gcttcttttc cagaatattg gttttttcaa     420
ttactatatg agcctctgat ctcctctgca cctcactttt ctctttccta ctccttttc     480 ctggagatat tgatgagtgc cgacggggcg tgcacagctg tggggaaaat gccacctgna     540
caaatatgga gggaaaccac acttgcacgt gtgctggcga cttgtctgag cctggacaga     600
tttgccctgg taggttggtg ggtggtttgg atccaagggg agggacttga ttcccaaaaa     660
atctctactt aagtgtgttt tcattagagc ttcaagaaat catttggttc aatcaggctg     720
gtgagtttcc tctcctgatt agattgatga taaggtcgag aatgaaatgg tccaagtttt     780
cttaatttaa tagcatctgg aataaatcct ttttattat tcacaatgca atataggtga     840
gaacacaggt ggttctcttt aactattcag ttaatgtcct gatttgtaat gttgatttkg     900
ggggccgctg ggagaacttg gcagggctag acaggttggg gaggatgtct ggtctgctgg     960
cattttgaat cactttcaag gatttttaaag tattacttta aaaagtcagt atttcttgag    1020
ctgaatgaga actttttaaa ttgttaatta tacccatttc tgcttcctga aacctccccc    1080
tgcaaaagca gtatcttctc accatcagca ctccagaatg gggaggggtg gtcagagggt    1140 ggcgggggt tggcttcaaa gacaccagaa gccagaatca gcttagtcac tgacagccat    1200
ttacccatct cagccctgca agcagaaaac atcctgaaaa aggaaaattc ggcacttgtt    1260
tggggctctg gttttcagt atattatttt ctcaaataat ttgctcttct tagaggtatt     1320
gaaaaactcc taatacttat gtagtcagct acacacccta atgtttttct tttaaagagc    1380
agcgaaccat taataaaaag ggactttttcc acttgggcat ccctctgtt atggtaacat    1440 ttcctctctg tcaaagttgc tagtcctgtc tttgagggct cccctgaaag ttaaatgcgt    1500
ttagaagcaa gtatcctgtg ggataaaatt ttgagactcc agggaactgg gggtaattga    1560
ctggatagtg gtgggtggtt acaagccatg aagagacg ttgttcagt gagaccctct       1620 taagctaact gttgttttac atggtgtgtt tttatagatg acagatggct tttataagag    1680
atctgtactc agggttcata tggtcttagg attgaccatt ctcttacttg cctccaatat    1740
actttatgtc aaatagtgct gaacctcaag caaaatgggt gactccatag caaattccat    1800
```

```
aaggtctggt taagaaagtg aaattattgt tccatatgac aaattgttca cagaaactag   1860
ttcctgatgt tgatatctga aagactccag tcacttcaga aagtaaaaga aatgcctttg   1920
attcttctag actctactct gctgtctcac cttgggaaga atggacacaa tttttttgaaa  1980
aaatgtttcc ctgaatatac cccgaatttt gaagggtact gcctcaatgg tcgtgtctgt   2040
atatattttg gcattgccaa cctgttctcc tgccagtaag tcaaactatt tttctgtaga   2100
gatatgatat tgcagcccat aagttttagt gaattcaaaa aatttatatt gagattttc    2160
tataattaaa cttttccata gtgaaaaata tatgtaattt atatatgtaa atctgggctt   2220
cccacatggt gcagcaataa agaatctgcc tgcccgtgca ggagaggcag gaaactcgga   2280
ttccgtgcct gggtcaggga agagcctctg gaggaggaag tascaaccca ttccagtatt   2340
cttcctgga ggtggagaga ggagcctagt gggcttacag tccatggggt cgcagagtct    2400
gacatgactg agcacacaca cacacgtaaa tctgttatt acatatatat atatatatat    2460
atatatataa aatgtgtgta ttacactctt tctgaatatt tcacacacac cccaggtgtc   2520
agtggcaaat atgaaattta aggaattggg tgatttcccc tctgacttaa ataacttgct   2580
gttactactg gtacagtctg ggaagtaaac tgagagaatt tcttaaaact tctatttat    2640
gccaaataga tgggagcat cagtgctgcg tttctaaatt ttaaaaagtg ttacatacag    2700
tcacactggg cctccatttt tctccctgta catcctaata gttggcgttt gcattttgt    2760
tgttaacaac tgataaatgc agccacggct gcctttgytc tgccttggtc accgtgatgg   2820
ctttggtggg ttatgtgtca gcctgctccc accatactcc ctcaaaaccg tgccctcag    2880
tctttagtaa aaccacaccc agaagatcta gttctgtatc aaatcttact tttagtaact  2940
ttcataatct gaaggcaatc tgagggaatg gatagatact gaaaaataaa taggtctctt   3000
ctggcyggcc tcctgactca gtgataattt tctctgtgcc taatgatgga gtgagagagt   3060
acgttgatcc tcataagtag gtgctataag cttaaaagct ttgattatta atcataatta   3120
gtagaaacat agtctaaatt actagaataa attatattct gtgatgaaga ctatggcctt   3180
gcattagaaa tcacatcatc ctgacaaaaa tagtgggaaa tgtttgtaaa tattagaaaa   3240
aataactcag tcctaataga aatctgtttt catattcata tttcatgcca tggttttcta   3300
acctaagata aatttagtac ttgatgataa tcattgttga ttttgataat aaggatcaaa   3360
ttgttttcat ctgttcatgg cttttttatta ttcccagtaa tgaaattatg aaaacaagta  3420
tcctagcaat ggtttatgtt tctctctgac actttaactt cggattatta aaggcattat   3480
aagaagaaga agggtactgc agagttatgt attgtagtta gcacatcaat ttcacttgga   3540
actgatagca ccaatcatta aatgtcttgt gaacactctt tagcacactg ctttcgtttc   3600
tgtcattaaa acccaatgaa aatatcatat tcctctaata atattttaaa tatgagttgc   3660
tacaaaatga caattaaact ggatctaaca cttaaattta agcacctttta atggcacccc  3720
actccagtac tcttacccgg aaaatcccat gcacagagga gcctggtaga ctgaaatcca   3780
tggggtcaca aagagtcaga catgactgag cgacttcact ttcacttttc actttcatgc   3840
attggaggag gaaatggcaa cccactccag tgttcctgcc tggagaatcc cagggacggg   3900
ggagcctggt gggctgccgt ctatggggtt gcacagagtc ggacrcgact gaagcgactt   3960
agcagcagca gcagcagcaa tcaaaagcaa tatttaaaat atcacctgag ttctcattaa   4020
tctggatcat aatttgtttt tgaattctat atctaataaa acatggatt tgtcagatat    4080
ccaacccttc catgccccag tgacctcacc ttgtattttt ttaattccat aaaaagaaaa   4140
```

```
catctctagg gagtgcttct cagtccaacg gttattagaa acatctcaca ggcatcattc    4200
tgcacatgta tacatgagtg ctaagttact tcagtcatgt tcaactctgt gcgaccctgt    4260
ggaccaygcc caccaagctc ctctgtccat gggattcttc aagcaagaat actagagtgg    4320
ttgcatgcct tcctccaggg gatcttccca ayccagggac tgaacccagg tcgtctgcat    4380
ctcctgcatt ggcaggtggg ttctctacca ctagcgccac ctgggaagcc cagagactgt    4440
tcacgatgtt gtgagcaggt tagtaaagga actttcttcc ttccttgctt ggaggcaatg    4500
gaagctcccc tcccagatgt aggaaatccc agctgccctg gggatgcaga ggatatgaga    4560
accggaagtc tctacaccac aggcctcctc agagggcccc tgctcggggg ttctcagagg    4620
attccaaacc tcttgagcac agaagaggtc ctcatttatt ctggtttggc tctgaaccaa    4680
cccacagcct ctagggcagg tcttcttcag cccaagttgc ccaaactatg gtgctgtgaa    4740
atgtttcatg agaaaaggat catgtggcac agtttaagaa atgctgctta cgctagcctt    4800
caattcttga ttcatggtca ccacaacgtg tgaaaaagtc ttgttgacct ttgtttagtc    4860
cagaacttga aattgtttga ccatggaacc aagcttattc ggctaggaaa ctttctgttt    4920
aatgtaggag aagaattaat caaaacccaa aaaattagtg atgtgtggcc tgcccttgtg    4980
aaatgctggc tgattgctct gggccttata aggctgaaag gctttgatat cgcagcctgc    5040
ttaactctcc agactcttat catgtgcttg acttattact tgagactttta tgatctctga    5100
gaggatcgga ggtgtggcct gttaatatcc accagtttaa aaatggctgc taggtgttaa    5160
taatggatgt gtataaccaa tgggttgttg ttaaaacatg tgttgttgtt aaatggatgt    5220
gttaaaacag catcagcaaa gccaggaata actggatggt cctccatggt gctatactca    5280
gatcgtgcat gctcttgcag agtcagaaca gtttttcaga ggtgcatgga actgaaaact    5340
cttttttggat gtggcccaac gtagtagaaa gaatacagac tttgaaatca gagaaccatt    5400
tgaatcaaaa ctaccattca ctaggcgtgt gacctggtac aaattatgta actccttttgc   5460
atctcacttt cctcatctat aaaatggaaa tctaccattg agaacaaaac aaaagtgccc    5520
agcgttcagc tgctgagtca tgtctgactc tttgcaaccc cgtggattgt agcatgccag    5580
gcccccctgt cctacactat ctcctggagt ttgctcagat tcatgtccct tgagtcggtg    5640
atgctatcta actatcccag tatcagaaac ataatgtgta tagcaaacgc tggtttcttt    5700
cccttctgtc tctgaaagtg acttgccaaa agctcctatg actaactcaa ggtacaacta    5760
ggactagact tgagatctct tctggggctt gatccatgca ggagatgcat gattcatcta    5820
aagcttgtcc cttgctgcct cttcccatca tggggactga tgtccattct ctgtgtattc    5880
ataccttcat ctccttctgg aataaagtgg gggcatgggt atatagttag tggatccagg    5940
gccaaggga agaaattcct aacaagtgag catcacaaaa tgcttagtag actatttcta    6000
aagtttatgc tcttctcaaag aataattaat tctactcaag atcctgagag gctctggaag    6060
catgcattcc cagtagatgg cagcatggtt tcatttactt tcacacaaaa gttcacagcc    6120
tgtgttggtt gctaatagtg ttagtcactc cgtcccatct tgtgtcttgg acttcttgag    6180
accccatgga ctgtagccca ccaggcttct ctgtccatgg gattcccag gcaagaatac    6240
tggagtaggt agccattccc ttcttcaacg tgtatcttcc caacccaggg atcgaaccca    6300
ggtctccatt acaggcagat actttatcta catatctaag ccaccaggga ggcccctat    6360
gaacaacaat aattccagta acagtttcac caatgaacag cgggatgttg gtgaatgccg    6420
cttttcccctc cacttagttt ttctctcttg aagaaagtaa gtgtgtgctt attgttacca    6480
ctgagacctt ttggatctat gacctttaag aaaaaaagtaa gaaaaatggt ttcctctgct    6540
```

```
tcctgttcag aggctactca cattctttta taacctggtc tcaagtaaaa gactctgctt    6600
tcaaattctt ccttcctttg acttatattg attgcaatct ggccaaacat ttgtttgtaa    6660
actccctttg ctcctagggc agggttgctt tgtgttggtc ttagagagag gcagttcttc    6720
ttttaacaga aattgattct taatcagtgt tctgcagtgc cttatagagg tggtatgcaa    6780
ataaccctga atcaatccct gggctcagtc atgtcagact aagtttatgc tgcagtaact    6840
tgtagatcag agtgctttca acttgacccg tttggcttcc tggggtgtca gcggtaaaga    6900
gacttgcctg ccagtacagg agacacggtt cgatccttgg gtcgggcaga tcccttgaag    6960
aaagaaatgg ccaacccatt ccagtatttt cttgcctgga aaatcccatg gacagaggag    7020
cctggtgggc tacagtccat ggggttgcaa gagtgggaca cagctgagtg actgaacaac    7080
agcagcaact gagccctgat ggattttcca tattcttcac aaagtatgag gctgaagtgt    7140
agaggctgag agatgactgg ctagtacaag aatgtaagtg tttctggcca tggctcactg    7200
ctgacttctg tctgtgtgtt gccgcagctg tcccattggc taccctggga agcgaggtga    7260
gtacatagac ttcgatgggt gggatccgca cagtgcaggc cgtgggcatc agtggaacac    7320
cagcccggtg gctgtccgtg cgctggtgct ggctttcctg ctgctcctcg ggctgtgcag    7380
agctcac                                                              7387
```

<210> SEQ ID NO 9
<211> LENGTH: 143
<212> TYPE: PRT
<213> ORGANISM: Bos taurus
<220> FEATURE:
<221> NAME/KEY: misc_feature
<222> LOCATION: (-41)..(-41)
<223> OTHER INFORMATION: The 'Xaa' at location -41 stands for a stop
      codon, Trp, or Cys.
<220> FEATURE:
<221> NAME/KEY: misc_feature
<222> LOCATION: (537)..()
<223> OTHER INFORMATION: TGN is Xaa, Xaa is probably selenocysteine
<220> FEATURE:
<221> NAME/KEY: misc_feature
<222> LOCATION: (537)..()
<223> OTHER INFORMATION: N is a, Xaa is probably selenocysteine
<220> FEATURE:
<221> NAME/KEY: misc_feature
<222> LOCATION: (7228)..()
<223> OTHER INFORMATION: mature protein ends at residue 7228

<400> SEQUENCE: 9

Asp Ile Asp Glu Cys Arg Arg Gly Val His Ser Cys Gly Glu Asn Ala
        -55                 -50                 -45

Thr Xaa Thr Asn Met Glu Gly Asn His Thr Cys Thr Cys Ala Gly Asp
    -40                 -35                 -30

Leu Ser Glu Pro Gly Gln Ile Cys Pro Asp Ser Thr Leu Leu Ser His
 -25                 -20                 -15

Leu Gly Lys Asn Gly His Asn Phe Leu Lys Lys Cys Phe Pro Glu Tyr
-10             -5                  -1  1                   5

Thr Pro Asn Phe Glu Gly Tyr Cys Leu Asn Gly Arg Val Cys Ile Tyr
            10                  15                  20

Phe Gly Ile Ala Asn Leu Phe Ser Cys His Cys Pro Ile Gly Tyr Pro
        25                  30                  35

Gly Lys Arg Gly Glu Tyr Ile Asp Phe Asp Gly Trp Asp Pro His Ser
    40                  45                  50

Ala Gly Arg Gly His Gln Trp Asn Thr Ser Pro Val Ala Val Arg Ala
55                  60                  65                  70

```
Leu Val Leu Ala Phe Leu Leu Leu Gly Leu Cys Arg Ala His
            75                  80                  85

<210> SEQ ID NO 10
<211> LENGTH: 159
<212> TYPE: DNA
<213> ORGANISM: Bos taurus
<220> FEATURE:
<221> NAME/KEY: mat_peptide
<222> LOCATION: (1)..()
<223> OTHER INFORMATION:
<220> FEATURE:
<221> NAME/KEY: CDS
<222> LOCATION: (1)..(159)
<223> OTHER INFORMATION:

<400> SEQUENCE: 10 aaa tgt ttc cct gaa tat acc ccg aat ttt gaa ggg tac tgc ctc aat      48
Lys Cys Phe Pro Glu Tyr Thr Pro Asn Phe Glu Gly Tyr Cys Leu Asn
1               5                   10                  15 ggt cgt gtc tgt ata tat ttt ggc att gcc aac ctg ttc tcc tgc cac      96
Gly Arg Val Cys Ile Tyr Phe Gly Ile Ala Asn Leu Phe Ser Cys His
            20                  25                  30 tgt ccc att ggc tac cct ggg aag cga ggt gag tac ata gac ttc gat     144
Cys Pro Ile Gly Tyr Pro Gly Lys Arg Gly Glu Tyr Ile Asp Phe Asp
        35                  40                  45 ggg tgg gat ccg cac                                                 159
Gly Trp Asp Pro His
    50

<210> SEQ ID NO 11
<211> LENGTH: 53
<212> TYPE: PRT
<213> ORGANISM: Bos taurus

<400> SEQUENCE: 11

Lys Cys Phe Pro Glu Tyr Thr Pro Asn Phe Glu Gly Tyr Cys Leu Asn
1               5                   10                  15

Gly Arg Val Cys Ile Tyr Phe Gly Ile Ala Asn Leu Phe Ser Cys His
            20                  25                  30

Cys Pro Ile Gly Tyr Pro Gly Lys Arg Gly Glu Tyr Ile Asp Phe Asp
        35                  40                  45

Gly Trp Asp Pro His
    50

<210> SEQ ID NO 12
<211> LENGTH: 19
<212> TYPE: DNA
<213> ORGANISM: Bos taurus

<400> SEQUENCE: 12
tggcaggaga acaggttgg                                                 19

<210> SEQ ID NO 13
<211> LENGTH: 18
<212> TYPE: DNA
<213> ORGANISM: Bos taurus

<400> SEQUENCE: 13
ctgtcccatt ggctaccc                                                  18

<210> SEQ ID NO 14
<211> LENGTH: 18
```

-continued

```
<212> TYPE: DNA
<213> ORGANISM: Bos taurus

<400> SEQUENCE: 14
gagctctgca cagcccga                                                18

<210> SEQ ID NO 15
<211> LENGTH: 35
<212> TYPE: DNA
<213> ORGANISM: Bos taurus

<400> SEQUENCE: 15
gccaacctgt tctcctgcca ctgtcccatt ggcta                              35

<210> SEQ ID NO 16
<211> LENGTH: 17
<212> TYPE: DNA
<213> ORGANISM: Bos taurus

<400> SEQUENCE: 16
gacggggcgt gcacagc                                                  17

<210> SEQ ID NO 17
<211> LENGTH: 408
<212> TYPE: DNA
<213> ORGANISM: Bos taurus
<220> FEATURE:
<221> NAME/KEY: misc_feature
<222> LOCATION: (36)..(36)
<223> OTHER INFORMATION: n is A, tga probably codes for selenocysteine
<220> FEATURE:
<221> NAME/KEY: misc_feature
<222> LOCATION: (-41)..(-41)
<223> OTHER INFORMATION: The 'Xaa' at location -41 is probably
      selenocysteine
<220> FEATURE:
<221> NAME/KEY: CDS
<222> LOCATION: (1)..(408)
<223> OTHER INFORMATION:
<220> FEATURE:
<221> NAME/KEY: mat_peptide
<222> LOCATION: (157)..()
<223> OTHER INFORMATION:
<220> FEATURE:
<221> NAME/KEY: misc_feature
<222> LOCATION: (331)..()
<223> OTHER INFORMATION: Mature peptide ends at position 331

<400> SEQUENCE: 17 cgg ggc gtg cac agc tgt ggg gaa aat gcc acc tgn aca aat atg gag    48
Arg Gly Val His Ser Cys Gly Glu Asn Ala Thr Xaa Thr Asn Met Glu
    -50                 -45                 -40 gga aac cac act tgc acg tgt gct ggc gac ttg tct gag cct gga cag    96
Gly Asn His Thr Cys Thr Cys Ala Gly Asp Leu Ser Glu Pro Gly Gln
-35                 -30                 -25 att tgc cct gac tct act ctg ctg tct cac ctt ggg aag aat gga cac   144
Ile Cys Pro Asp Ser Thr Leu Leu Ser His Leu Gly Lys Asn Gly His
-20                 -15                 -10                  -5 aat ttt ttg aaa aaa tgt ttc cct gaa tat acc ccg aat ttt gaa ggg   192
Asn Phe Leu Lys Lys Cys Phe Pro Glu Tyr Thr Pro Asn Phe Glu Gly
         -1  1                   5                  10 tac tgc ctc aat ggt cag gtc tgt ata tat ttt ggc att gcc aac ctg   240
Tyr Cys Leu Asn Gly Gln Val Cys Ile Tyr Phe Gly Ile Ala Asn Leu
             15                  20                  25 ttc tcc tgc caa tgt ccc att ggc tac cct ggg aag cga ggt gag tac   288
Phe Ser Cys Gln Cys Pro Ile Gly Tyr Pro Gly Lys Arg Gly Glu Tyr
30                  35                  40
```

```
ata gac ttc gat ggg tgg gat ccg cac agt gca ggc cgt ggg cat cag    336
Ile Asp Phe Asp Gly Trp Asp Pro His Ser Ala Gly Arg Gly His Gln
 45              50                  55                  60 tgg aac acc agc ccg gtg gct gtc cgt gcg ctg gtg ctg gct ttc ctg    384
Trp Asn Thr Ser Pro Val Ala Val Arg Ala Leu Val Leu Ala Phe Leu
             65                  70                  75 ctg ctc ctc ggg ctg tgc aga gct                                    408
Leu Leu Leu Gly Leu Cys Arg Ala
             80
```

<210> SEQ ID NO 18
<211> LENGTH: 136
<212> TYPE: PRT
<213> ORGANISM: Bos taurus
<220> FEATURE:
<221> NAME/KEY: misc_feature
<222> LOCATION: (-41)..(-41)
<223> OTHER INFORMATION: The 'Xaa' at location -41 stands for a stop
    codon, Trp, or Cys.
<220> FEATURE:
<221> NAME/KEY: misc_feature
<222> LOCATION: (36)..(36)
<223> OTHER INFORMATION: n is A, tga probably codes for selenocysteine
<220> FEATURE:
<221> NAME/KEY: misc_feature
<222> LOCATION: (331)..()
<223> OTHER INFORMATION: Mature peptide ends at position 331

<400> SEQUENCE: 18

```
Arg Gly Val His Ser Cys Gly Glu Asn Ala Thr Xaa Thr Asn Met Glu
        -50                 -45                 -40

Gly Asn His Thr Cys Thr Cys Ala Gly Asp Leu Ser Glu Pro Gly Gln
        -35                 -30                 -25

Ile Cys Pro Asp Ser Thr Leu Leu Ser His Leu Gly Lys Asn Gly His
-20                 -15                 -10                  -5

Asn Phe Leu Lys Lys Cys Phe Pro Glu Tyr Thr Pro Asn Phe Glu Gly
         -1  1                  5                  10

Tyr Cys Leu Asn Gly Gln Val Cys Ile Tyr Phe Gly Ile Ala Asn Leu
         15                  20                  25

Phe Ser Cys Gln Cys Pro Ile Gly Tyr Pro Gly Lys Arg Gly Glu Tyr
     30                  35                  40

Ile Asp Phe Asp Gly Trp Asp Pro His Ser Ala Gly Arg Gly His Gln
 45                  50                  55                  60

Trp Asn Thr Ser Pro Val Ala Val Arg Ala Leu Val Leu Ala Phe Leu
             65                  70                  75

Leu Leu Leu Gly Leu Cys Arg Ala
             80
```

<210> SEQ ID NO 19
<211> LENGTH: 43
<212> TYPE: DNA
<213> ORGANISM: Bos taurus

<400> SEQUENCE: 19
ggcatgcata gaaggaagaa aatgtttccc tgaatatacc ccg                    43

<210> SEQ ID NO 20
<211> LENGTH: 27
<212> TYPE: DNA
<213> ORGANISM: Bos taurus

<400> SEQUENCE: 20

-continued caagcttagt gcggatccca cccatcg        27

<210> SEQ ID NO 21
<211> LENGTH: 37
<212> TYPE: DNA
<213> ORGANISM: Bos taurus

<400> SEQUENCE: 21
gctcgagaaa agaaaatgtt tccctgaata taccccg        37

<210> SEQ ID NO 22
<211> LENGTH: 43
<212> TYPE: DNA
<213> ORGANISM: Bos taurus

<400> SEQUENCE: 22
gctcgaggcc gccatggcca aatgtttccc tgaatatacc ccg        43

<210> SEQ ID NO 23
<211> LENGTH: 46
<212> TYPE: DNA
<213> ORGANISM: Bos taurus

<400> SEQUENCE: 23
cctctagatt tcgccttct atgtgcggat cccacccatc gaagtc        46

<210> SEQ ID NO 24
<211> LENGTH: 435
<212> TYPE: DNA
<213> ORGANISM: Mus musculus
<300> PUBLICATION INFORMATION:
<301> AUTHORS: Gray, A., Dull, T.J. and Ullrich, A.
<302> TITLE: Nucleotide sequence of epidermal growth factor cDNA
       predicts a 128,000-molecular weight protein precursor
<303> JOURNAL: Nature
<304> VOLUME: 303
<306> PAGES: 722-725
<307> DATE: 1983
<308> DATABASE ACCESSION NUMBER: GenBank Accession No. J00380
<309> DATABASE ENTRY DATE: 1993-04-27
<313> RELEVANT RESIDUES: Relevant residues FROM 3108 TO 3539

<400> SEQUENCE: 24
gatattgacg agtgccagcg gggggcgcac aactgcgctg agaatgccgc ctgcaccaac        60
acggagggag gctacaactg cacctgcgca ggccgcccat cctcgcccgg acggagttgc       120
cctgactcta ccgcaccctc tctccttggg aagatggcc accatttgga ccgaaatagt       180
tatccaggat gcccatcctc atatgatgga tactgcctca atggtggcgt gtgcatgcat       240
attgaatcac tggacagcta cacatgcaac tgtgttattg ctattctggg ggatcgatgt       300
cagactcgag acctacgatg gtgggagctg cgtcatgctg gctacgggca gaagcatgac       360
atcatggtgg tggctgtctg catggtgtca ctggtcctgc tgctcctctt ggggatgtgg       420
gggacttact actac       435

<210> SEQ ID NO 25
<211> LENGTH: 435
<212> TYPE: DNA
<213> ORGANISM: Sus scrofa
<300> PUBLICATION INFORMATION:
<301> AUTHORS: Kim, J.G., Vallet, J.L. and Christenson, R.K.
<302> TITLE: Characterization of uterine epidermal growth factor
       during pregnancy in pigs.
<303> JOURNAL: unpublished
<307> DATE: 2001
<308> DATABASE ACCESSION NUMBER: GenBank Accession No. AF336151

<309> DATABASE ENTRY DATE: 2001-03-14
<313> RELEVANT RESIDUES: Relevant residues FROM 3172 TO 3606

<400> SEQUENCE: 25

| | | | | | |
|---|---|---|---|---|---|
| gatattgatg | agtgccaact | aggtgtgcac | acctgtgggg | aaaatgccac | ctgtacaaat | 60 |
| acggagggaa | actacacctg | cacatgtgct | ggccgcccct | ctgaacccgg | acggatttgc | 120 |
| cctgacccta | ctccaccctc | tcacctcggg | gaggatggcc | gctattctgt | gagaaatagt | 180 |
| tactctgaat | gcccgccgtc | ccacgacggg | tactgcctcc | acggtggtgt | gtgtatgtat | 240 |
| attgaagccg | tcgacagcta | tgcctgcaac | tgtgtttttg | gctacgttgg | cgagcgatgt | 300 |
| cagcacagag | acttgaaatg | gtgggagctg | cgccacgctg | gcctcgggcg | acagtggaac | 360 |
| gtcacggtgg | tggccgtctg | cgtggtggtg | ctggtcctgc | tgctgctcct | ggggctgtgg | 420 |
| ggggctcact | actac | | | | | 435 |

<210> SEQ ID NO 26
<211> LENGTH: 438
<212> TYPE: DNA
<213> ORGANISM: Homo sapiens
<300> PUBLICATION INFORMATION:
<301> AUTHORS: Bell, G.I., Fong, N.M., Stempien, M.M., Wormsted, M.A.,
    Caput, D., Ku, L.L., Urdea, M.S., Rall, L.B. and Sanchez-
    Pescador, R.
<302> TITLE: Human epidermal growth factor precursor: cDNA sequence,
    expression in vitro and gene organization.
<303> JOURNAL: Nucleic Acids Research
<304> VOLUME: 14
<305> ISSUE: 21
<306> PAGES: 8427-8446
<307> DATE: 1986
<308> DATABASE ACCESSION NUMBER: GenBank Accession No. X04571
<309> DATABASE ENTRY DATE: 1993-04-21
<313> RELEVANT RESIDUES: Relevant residues FROM 3170 TO 3607

<400> SEQUENCE: 26

| | | | | | |
|---|---|---|---|---|---|
| gatattgatg | agtgccaact | ggggtgcac | agctgtggag | agaatgccag | ctgcacaaat | 60 |
| acagagggag | gctataccctg | catgtgtgct | ggacgcctgt | ctgaaccagg | actgatttgc | 120 |
| cctgactcta | ctccaccccc | tcacctcagg | gaagatgacc | accactattc | cgtaagaaat | 180 |
| agtgactctg | aatgtcccct | gtcccacgat | gggtactgcc | tccatgatgg | tgtgtgcatg | 240 |
| tatattgaag | cattggacaa | gtatgcatgc | aactgtgttg | ttggctacat | cggggagcga | 300 |
| tgtcagtacc | gagacctgaa | gtggtgggaa | ctgcgccacg | ctggccacgg | gcagcagcag | 360 |
| aaggtcatcg | tggtggctgt | ctgcgtggtg | gtgcttgtca | tgctgctcct | cctgagcctg | 420 |
| tgggggggccc | actactac | | | | | 438 |

<210> SEQ ID NO 27
<211> LENGTH: 159
<212> TYPE: DNA
<213> ORGANISM: Mus musculus
<300> PUBLICATION INFORMATION:
<301> AUTHORS: Gray, A., Dull, T.J. and Ullrich, A.
<302> TITLE: Nucleotide sequence of epidermal growth factor cDNA
    predicts a 128,000-molecular weight protein precursor
<303> JOURNAL: Nature
<304> VOLUME: 303
<306> PAGES: 722-725
<307> DATE: 1983
<308> DATABASE ACCESSION NUMBER: GenBank Accession No. J00380
<309> DATABASE ENTRY DATE: 1993-04-27
<313> RELEVANT RESIDUES: Relevant residues FROM 3282 TO 3440

<400> SEQUENCE: 27

| | | | | | |
|---|---|---|---|---|---|
| aatagttatc | caggatgccc | atcctcatat | gatggatact | gcctcaatgg | tggcgtgtgc | 60 |

-continued

```
atgcatattg aatcactgga cagctacaca tgcaactgtg ttattggcta ttctggggat    120
cgatgtcaga ctcgagacct acgatggtgg gagctgcgt                           159
```

<210> SEQ ID NO 28
<211> LENGTH: 159
<212> TYPE: DNA
<213> ORGANISM: Sus scrofa
<300> PUBLICATION INFORMATION:
<301> AUTHORS: Kim, J.G., Vallet, J.L. and Christenson, R.K.
<302> TITLE: Characterization of uterine epidermal growth factor during
      pregnancy in pigs.
<303> JOURNAL: unpublished
<307> DATE: 2001
<308> DATABASE ACCESSION NUMBER: GenBank Accession No. AF336151
<309> DATABASE ENTRY DATE: 2001-03-14
<313> RELEVANT RESIDUES: Relevant residues FROM 3346 TO 3504

<400> SEQUENCE: 28

```
aatagttact ctgaatgccc gccgtcccac gacgggtact gcctccacgg tggtgtgtgt    60
atgtatattg aagccgtcga cagctatgcc tgcaactgtg tttttggcta cgttggcgag    120
cgatgtcagc acagagactt gaaatggtgg gagctgcgc                           159
```

<210> SEQ ID NO 29
<211> LENGTH: 159
<212> TYPE: DNA
<213> ORGANISM: Homo sapiens
<300> PUBLICATION INFORMATION:
<301> AUTHORS: Bell, G.I., Fong, N.M., Stempien, M.M., Wormsted, M.A.,
      Caput, D., Ku, L.L., Urdea, M.S., Rall, L.B. and Sanchez-
      Pescador, R.
<302> TITLE: Human epidermal growth factor precursor: cDNA sequence,
      expression in vitro and gene organization.
<303> JOURNAL: Nucleic Acids Research
<304> VOLUME: 14
<305> ISSUE: 21
<306> PAGES: 8427-8446
<307> DATE: 1986
<308> DATABASE ACCESSION NUMBER: GenBank Accession No. X04571
<309> DATABASE ENTRY DATE: 1993-04-21
<313> RELEVANT RESIDUES: Relevant residues FROM 3347 TO 3505

<400> SEQUENCE: 29

```
aatagtgact ctgaatgtcc cctgtcccac gatgggtact gcctccatga tggtgtgtgc    60
atgtatattg aagcattgga caagtatgca tgcaactgtg ttgttggcta catcggggag    120
cgatgtcagt accgagacct gaagtggtgg gaactgcgc                           159
```

<210> SEQ ID NO 30
<211> LENGTH: 145
<212> TYPE: PRT
<213> ORGANISM: Mus musculus
<300> PUBLICATION INFORMATION:
<301> AUTHORS: Gray, A., Dull, T.J. and Ullrich, A.
<302> TITLE: Nucleotide sequence of epidermal growth factor cDNA
      predicts a 128,000-molecular weight protein precursor
<303> JOURNAL: Nature
<304> VOLUME: 303
<306> PAGES: 722-725
<307> DATE: 1983
<308> DATABASE ACCESSION NUMBER: GenBank Accession No. J00380
<309> DATABASE ENTRY DATE: 1993-04-27
<313> RELEVANT RESIDUES: Relevant residues FROM 919 TO 1063

<400> SEQUENCE: 30

```
Asp Ile Asp Glu Cys Gln Arg Gly Ala His Asn Cys Ala Glu Asn Ala
 1               5                  10                  15

Ala Cys Thr Asn Thr Glu Gly Gly Tyr Asn Cys Thr Cys Ala Gly Arg
```

```
              20                  25                  30
Pro Ser Ser Pro Gly Arg Ser Cys Pro Asp Ser Thr Ala Pro Ser Leu
        35                  40                  45
Leu Gly Glu Asp Gly His His Leu Asp Arg Asn Ser Tyr Pro Gly Cys
    50                  55                  60
Pro Ser Ser Tyr Asp Gly Tyr Cys Leu Asn Gly Val Cys Met His
65                  70                  75                  80
Ile Glu Ser Leu Asp Ser Tyr Thr Cys Asn Cys Val Ile Gly Tyr Ser
                85                  90                  95
Gly Asp Arg Cys Gln Thr Arg Asp Leu Arg Trp Trp Glu Leu Arg His
            100                 105                 110
Ala Gly Tyr Gly Gln Lys His Asp Ile Met Val Val Ala Val Cys Met
            115                 120                 125
Val Ser Leu Val Leu Leu Leu Leu Gly Met Trp Gly Thr Tyr Tyr
        130                 135                 140
Tyr
145

<210> SEQ ID NO 31
<211> LENGTH: 145
<212> TYPE: PRT
<213> ORGANISM: Sus scrofa
<300> PUBLICATION INFORMATION:
<301> AUTHORS: Kim, J.G., Vallet, J.L. and Christenson, R.K.
<302> TITLE: Characterization of uterine epidermal growth factor
       during pregnancy in pigs.
<303> JOURNAL: unpublished
<307> DATE: 2001
<308> DATABASE ACCESSION NUMBER: GenBank Accession No. AF336151
<309> DATABASE ENTRY DATE: 2001-03-14
<313> RELEVANT RESIDUES: Relevant residues FROM 912 TO 1056

<400> SEQUENCE: 31

Asp Ile Asp Glu Cys Gln Leu Gly Val His Thr Cys Gly Glu Asn Ala
 1               5                  10                  15
Thr Cys Thr Asn Thr Glu Gly Asn Tyr Thr Cys Thr Cys Ala Gly Arg
            20                  25                  30
Pro Ser Glu Pro Gly Arg Ile Cys Pro Asp Pro Thr Pro Ser His
        35                  40                  45
Leu Gly Glu Asp Gly Arg Tyr Ser Val Arg Asn Ser Tyr Ser Glu Cys
    50                  55                  60
Pro Pro Ser His Asp Gly Tyr Cys Leu His Gly Val Cys Met Tyr
65                  70                  75                  80
Ile Glu Ala Val Asp Ser Tyr Ala Cys Asn Cys Val Phe Gly Tyr Val
                85                  90                  95
Gly Glu Arg Cys Gln His Arg Asp Leu Lys Trp Trp Glu Leu Arg His
            100                 105                 110
Ala Gly Leu Gly Arg Gln Trp Asn Val Thr Val Val Ala Val Cys Val
            115                 120                 125
Val Val Leu Val Leu Leu Leu Leu Gly Leu Trp Gly Ala His Tyr
        130                 135                 140
Tyr
145

<210> SEQ ID NO 32
<211> LENGTH: 146
<212> TYPE: PRT
<213> ORGANISM: Homo sapiens
<300> PUBLICATION INFORMATION:
```

<301> AUTHORS: Bell, G.I., Fong, N.M., Stempien, M.M., Wormsted, M.A., Caput, D., Ku, L.L., Urdea, M.S., Rall, L.B. and Sanchez-Pescador, R.
<302> TITLE: Human epidermal growth factor precursor: cDNA sequence, expression in vitro and gene organization.
<303> JOURNAL: Nucleic Acids Research
<304> VOLUME: 14
<305> ISSUE: 21
<306> PAGES: 8427-8446
<307> DATE: 1986
<308> DATABASE ACCESSION NUMBER: GenBank Accession No. X04571
<309> DATABASE ENTRY DATE: 1993-04-21
<313> RELEVANT RESIDUES: Relevant residues FROM 912 TO 1057

<400> SEQUENCE: 32

Asp Ile Asp Glu Cys Gln Leu Gly Val His Ser Cys Gly Glu Asn Ala
 1               5                  10                  15

Ser Cys Thr Asn Thr Glu Gly Gly Tyr Thr Cys Met Cys Ala Gly Arg
            20                  25                  30

Leu Ser Glu Pro Gly Leu Ile Cys Pro Asp Ser Thr Pro Pro Pro His
        35                  40                  45

Leu Arg Glu Asp Asp His His Tyr Ser Val Arg Asn Ser Asp Ser Glu
    50                  55                  60

Cys Pro Leu Ser His Asp Gly Tyr Cys Leu His Asp Gly Val Cys Met
65                  70                  75                  80

Tyr Ile Glu Ala Leu Asp Lys Tyr Ala Cys Asn Cys Val Val Gly Tyr
                85                  90                  95

Ile Gly Glu Arg Cys Gln Tyr Arg Asp Leu Lys Trp Trp Glu Leu Arg
            100                 105                 110

His Ala Gly His Gly Gln Gln Gln Lys Val Ile Val Val Ala Val Cys
        115                 120                 125

Val Val Val Leu Val Met Leu Leu Leu Ser Leu Trp Gly Ala His
    130                 135                 140

Tyr Tyr
145

<210> SEQ ID NO 33
<211> LENGTH: 53
<212> TYPE: PRT
<213> ORGANISM: Mus musculus
<300> PUBLICATION INFORMATION:
<301> AUTHORS: Gray, A., Dull, T.J. and Ullrich, A.
<302> TITLE: Nucleotide sequence of epidermal growth factor cDNA predicts a 128,000-molecular weight protein precursor
<303> JOURNAL: Nature
<304> VOLUME: 303
<306> PAGES: 722-725
<307> DATE: 1983
<308> DATABASE ACCESSION NUMBER: GenBank Accession No. J00380
<309> DATABASE ENTRY DATE: 1993-04-27
<313> RELEVANT RESIDUES: Relevant residues FROM 977 TO 1029

<400> SEQUENCE: 33

Asn Ser Tyr Pro Gly Cys Pro Ser Ser Tyr Asp Gly Tyr Cys Leu Asn
 1               5                  10                  15

Gly Gly Val Cys Met His Ile Glu Ser Leu Asp Ser Tyr Thr Cys Asn
            20                  25                  30

Cys Val Ile Gly Tyr Ser Gly Asp Arg Cys Gln Thr Arg Asp Leu Arg
        35                  40                  45

Trp Trp Glu Leu Arg
    50

<210> SEQ ID NO 34

```
<211> LENGTH: 53
<212> TYPE: PRT
<213> ORGANISM: Sus scrofa
<300> PUBLICATION INFORMATION:
<301> AUTHORS: Kim, J.G., Vallet, J.L. and Christenson, R.K.
<302> TITLE: Characterization of uterine epidermal growth factor
       during pregnancy in pigs.
<303> JOURNAL: unpublished
<307> DATE: 2001
<308> DATABASE ACCESSION NUMBER: GenBank Accession No. AF336151
<309> DATABASE ENTRY DATE: 2001-03-14
<313> RELEVANT RESIDUES: Relevant residues FROM 970 TO 1022

<400> SEQUENCE: 34

Asn Ser Tyr Ser Glu Cys Pro Pro Ser His Asp Gly Tyr Cys Leu His
 1               5                  10                  15

Gly Gly Val Cys Met Tyr Ile Glu Ala Val Asp Ser Tyr Ala Cys Asn
            20                  25                  30

Cys Val Phe Gly Tyr Val Gly Glu Arg Cys Gln His Arg Asp Leu Lys
        35                  40                  45

Trp Trp Glu Leu Arg
    50

<210> SEQ ID NO 35
<211> LENGTH: 53
<212> TYPE: PRT
<213> ORGANISM: Homo sapiens
<300> PUBLICATION INFORMATION:
<301> AUTHORS: Bell, G.I., Fong, N.M., Stempien, M.M., Wormsted, M.A.,
       Caput, D., Ku, L.L., Urdea, M.S., Rall, L.B. and Sanchez-
       Pescador, R.
<302> TITLE: Human epidermal growth factor precursor: cDNA sequence,
       expression in vitro and gene organization.
<303> JOURNAL: Nucleic Acids Research
<304> VOLUME: 14
<305> ISSUE: 21
<306> PAGES: 8427-8446
<307> DATE: 1986
<308> DATABASE ACCESSION NUMBER: GenBank Accession No. X04571
<309> DATABASE ENTRY DATE: 1993-04-21
<313> RELEVANT RESIDUES: Relevant residues FROM 970 TO 1022

<400> SEQUENCE: 35

Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 36
<211> LENGTH: 135
<212> TYPE: DNA
<213> ORGANISM: Bos taurus

<400> SEQUENCE: 36 aac cac act tgc acg tgt gct ggc gac ttg tct gag cct gga cag att    48
Asn His Thr Cys Thr Cys Ala Gly Asp Leu Ser Glu Pro Gly Gln Ile
 1               5                  10                  15 tgc cct gac tct act ctg ctg tct cac ctt ggg aag aat gga cac aat    96
Cys Pro Asp Ser Thr Leu Leu Ser His Leu Gly Lys Asn Gly His Asn
            20                  25                  30 ttt ttg aaa aaa tgt ttc cct gaa tat acc ccg aat ttt               135
Phe Leu Lys Lys Cys Phe Pro Glu Tyr Thr Pro Asn Phe
```

```
                    35                  40                  45

<210> SEQ ID NO 37
<211> LENGTH: 45
<212> TYPE: PRT
<213> ORGANISM: Bos taurus

<400> SEQUENCE: 37

Asn His Thr Cys Thr Cys Ala Gly Asp Leu Ser Glu Pro Gly Gln Ile
1               5                   10                  15

Cys Pro Asp Ser Thr Leu Leu Ser His Leu Gly Lys Asn Gly His Asn
            20                  25                  30

Phe Leu Lys Lys Cys Phe Pro Glu Tyr Thr Pro Asn Phe
        35                  40                  45
```

We claim:

1. An isolated nucleic acid encoding a polypeptide, wherein the encoded polypeptide comprises an amino acid sequence selected from the group consisting of
    a) an amino acid sequence depicted in SEQ ID NO: 9;
    b) an amino acid sequence depicted in SEQ ID NO: 11; and
    c) an amino acid sequence having at least 99% homology to the amino acid sequence depicted in SEQ ID NO: 9 or to the amino acid sequence depicted in SEQ ID NO: 11.

2. The isolated nucleic acid as set forth in claim 1, wherein the nucleic acid comprises the nucleotide sequence selected from the group consisting of
    a) a nucleotide sequence depicted in SEQ ID NO: 8; and
    b) a nucleotide sequence depicted in SEQ ID NO: 10.

3. An expression construct capable of directing the expression of a polypeptide in a suitable host cell, wherein the expression construct comprises a nucleic acid as set forth in claim 1 operably linked to control sequences compatible with the host cell.

4. A vector comprising a nucleic acid as set forth in claim 1.

5. An isolated host cell comprising a nucleic acid as set forth in claim 1, so that the cell can express a polypeptide encoded by the nucleic acid.

6. The host cell according to claim 5, wherein the cell is selected from *Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Escherichia coli, Bacillus subtilis* and *Bacillus licheniformis*, or a plant cell.

7. The host cell as set forth in claim 6, wherein the cell is *Escherichia coli*.

8. The host cell as set forth in claim 6, wherein the cell is *Pichia pastoris*.

9. A feed additive comprising a microorganism or a plant tissue, wherein the microorganism or plant tissue expresses a polypeptide encoded by a nucleic acid, wherein the encoded polypeptide comprises an amino acid sequence selected from the group consisting of
    a) an amino acid sequence depicted in SEQ ID NO: 9;
    b) an amino acid sequence depicted in SEQ ID NO: 11; and
    c) an amino acid sequence having at least 99% homology to the amino acid sequence depicted in SEQ ID NO: 9 or to the amino acid sequence depicted in SEQ ID NO: 11.

10. The feed additive as set forth in claim 9, wherein the microorganism is selected from *Aspergillus niger, Aspergillus ficuum, Aspergillus awamori, Aspergillus oryzae, Trichoderma reesei, Mucor miehei, Pichia pastoris, Saccharomyces cerevisiae, Escherichia coli, Bacillus subtilis* and *Bacillus licheniformis*.

11. The feed additive as set forth in claim 10, wherein the microorganism is *Escherichia coli*.

12. The feed additive as set forth in claim 10, wherein the microorganism is *Pichia pastoris*.

13. A method for producing a polypeptide comprising the steps of:
    a) culturing a host cell comprising a nucleic acid encoding a polypeptide, wherein the encoded polypeptide comprises an amino acid sequence selected from the group consisting of
        i) an amino acid sequence depicted in SEQ ID NO: 9;
        ii) an amino acid sequence depicted in SEQ ID NO: 11, and
        iii) an amino acid sequence having at least 99% homology to the amino acid sequence depicted in SEQ ID NO:9 or to the amino acid sequence depicted in SEQ ID NO:11, under conditions conducive to the expression of the polypeptide encoded by the nucleic acid; and
    b) recovering the encoded polypeptide from the host cell, from the culture medium comprising the host cell, or from an extract obtained from the host cell.

14. The method as set forth in claim 13, wherein the host cell is selected from *Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Escherichia coli, Bacillus subtilis* and *Bacillus licheniformis*, or a plant cell.

15. The method as set forth in claim 14, wherein the host cell is *Escherichia coli*.

16. The method as set forth in claim 15, wherein the host cell is *Pichia pastoris*.

* * * * *